(12) United States Patent  
Sevick-Muraca et al.

(10) Patent No.: US 7,187,441 B1  
(45) Date of Patent: *Mar. 6, 2007

(54) PARTICLE ANALYSIS SYSTEM AND METHOD

(75) Inventors: Eva Sevick-Muraca, Lafayette, IN (US); Joseph Pierce, Appleton, WI (US); Steven Richter, Brunswick, GA (US); Rajesh Shinde, West Lafayette, IN (US); Ganesh Balgi, Lebanon, IN (US); Jeffrey Kao, Lake Jackson, TX (US); Huabei Jiang, Clemson, SC (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/297,895

(22) PCT Filed: Nov. 7, 1997

(86) PCT No.: PCT/US97/20539

§ 371 (c)(1),  
(2), (4) Date: Jun. 30, 1999

(87) PCT Pub. No.: WO98/20323

PCT Pub. Date: May 14, 1998

Related U.S. Application Data

(63) Continuation-in-part of application No. 08/747,112, filed on Nov. 8, 1996, now Pat. No. 5,818,583.
(60) Provisional application No. 60/050,809, filed on Jun. 26, 1997.

(51) Int. Cl.  
*G01N 21/51* (2006.01)
(52) U.S. Cl. ...................... 356/336; 356/342
(58) Field of Classification Search ............... 356/335, 356/336, 342  
See application file for complete search history.

(56) References Cited

U.S. PATENT DOCUMENTS 4,245,909 A     1/1981  Loos .......................... 356/336

(Continued)

FOREIGN PATENT DOCUMENTS

WO         WO 95/12132         5/1995

OTHER PUBLICATIONS

*Measurement of Particle-Size Distribution and Volume Fraction in concentrated Suspension with Photon Migration Techniques*, Jiang, Pierce, Kao, Sevick Muraca, Applied Optics, vol. 36, No. 15/20 May 1997.

(Continued)

*Primary Examiner*—Richard A. Rosenberger  
(74) *Attorney, Agent, or Firm*—Baker Botts L.L.P.

(57) ABSTRACT

A system (20) and method are disclosed for the self-calibrating, on-line determination of size distribution f(x) and volume fraction φ of a number of particles (P) dispersed in a medium (M) by detecting one or more propagation characteristics of multiply scattered light from the particles (P). The multiply scattered light is re-emitted in response to exposure to a light source (21) configured to provide light at selected wavelengths. The determination includes calculating the isotropic scattering and absorption coefficients for the particles (P) by comparing the incident and detected light to determine a measurement corresponding to the propagation time through the scattering medium (M), and iteratively estimating the size distribution f(x) and volume fraction φ as a function of the coefficients for each of the wavelengths. An estimation approach based on an expected form of the distribution and the mass of the particles is also disclosed. Furthermore, techniques to determine a particle structure factor indicative of particle-to-particle interactions which vary with particle concentration and influence light scattering at high concentrations is disclosed.

48 Claims, 22 Drawing Sheets

U.S. PATENT DOCUMENTS

| | | | |
|---|---|---|---|
| 4,497,577 A * | 2/1985 | Sato et al. | 356/336 |
| 4,641,969 A | 2/1987 | Lundberg et al. | 356/343 |
| 4,781,460 A | 11/1988 | Bott | 356/336 |
| 4,871,251 A | 10/1989 | Preikschat et al. | 356/336 |
| 4,890,920 A | 1/1990 | Niziolek et al. | 356/336 |
| 5,164,787 A | 11/1992 | Igushi et al. | 356/336 |
| 5,229,839 A | 7/1993 | Hayashi et al. | 356/336 |
| 5,353,799 A | 10/1994 | Chance | |
| 5,416,580 A | 5/1995 | Trainer | 356/336 |
| 5,424,843 A | 6/1995 | Tromberg et al. | 356/442 |
| 5,438,408 A | 8/1995 | Weichert et al. | 356/336 |
| 5,455,675 A | 10/1995 | Witt et al. | 356/336 |
| 5,502,561 A | 3/1996 | Hutchins et al. | 356/336 |
| 5,619,324 A | 4/1997 | Harvill et al. | 356/336 |
| 5,818,583 A | 10/1998 | Sevick-Muraca et al. | 356/336 |
| 5,865,754 A | 2/1999 | Sevick-Muraca et al. | 600/476 |

OTHER PUBLICATIONS

*Frequency-Domain Photon Migration Techniques for On-Line Measurement of Particle Size Distribution and Volume Fraction in Concentrated Process Streams*, Jiang, Pierce, Kao, Sevick-Muraca, SPIE vol. 3000.

*Frequency-Domain Method for Measuring Spectral Porperties in Multiple-Scattering Media: Methemoglobin Absorption Spectrum in a Tissuelike Phanton*, Fishkin, So, Cerussi, Fantini, Franceschini, Gratton, Applied Optics, vol. 34, No. 6, Mar. 1, 1995.

Huabel Jiang, Keith D. Paulsen, Ulf L. Osterberg, Brian W. Pogue and Michael S. Patterson, *Optical Image Reconstruction Using Frequency-Domain Data: Simulations and Experiments*, Journal of the Optical Society of America, Sep. 1995, at 253.

Alwin Kienle, Lothar Lilge, Michael S. Patterson, Raimund Hibst, Rudolf Steiner, and Brian C. Wilson, *Spatially Resolved Absolute Diffuse Relectance Measurements for Noninvasive Determination of the Optical Scattering and Absorption Coefficients of Biological Tissue*, Applied Optics, May 1996, vol. 35, No. 13 at 2304.

Pi-Huan Wang, Geoffrey S. Kent, M. Patrick McCormick, Larry W. Thomason, and Glenn K. Yue, *Retrieval Analysis of Aerosol-Size Distribution with Simulated Extinction Measurements at SAGE III Wavelengths*, Applied Optics, Jan. 1996, vol. 35, No. 3, at 433.

Kusiel S. Shifrin and Ilja G. Zolotov, *Spectral Attenuation and Aerosol Particle Size Distribution*, Applied Optics, Apr. 1996, vol. 35, No. 12, at 2114.

Jianhong Wang and F. Ross Hallett, *Spherical Particle Size Determination by Analytical Inversion of the UV-Visible-NIR Extinction Spectrum*, Applied Optics, Jan. 1996, vol. 35, No. 1, at 193.

Sergei A. Vinogradov, Leu-Wei Lo, William T. Jenkins, Sydney M. Evans, Cameron Koch, and David F. Wilson, *Noninvasive Imaging of the Distribution in Oxygen in Tissue in Vivo Using Near-Infrared Phosphors*, Biophysical Journal, Apr. 1996. vol. 70, at 1609-1617.

Joshua B. Fishkin, Peter T.C. So, Albert E. Cerussi, Sergio Fantini, Maria Angela Franceschini, and Enrico Gratton, *Frequency-Domain Method for Measuring Spectral Properties in Multiple-Scattering Media: Methemoglobin Absorption Spectrum in a Tissuelike Phantom*, Applied Optics, Mar. 1995, vol. 34, No. 7, at 1143.

Heimo Schnablegger and Otto Glatter, *Sizing of Colloidal Particles with Light Scattering: Corrections for Beginning Multiple Scattering*, Applied Optics, Jun. 1995, vol. 34, No. 18, at 3489.

Robert J. Farrell and Yen-Cheng Tsai, *Nonlinear Controller for Batch Crystallization: Development and Experimental Demonstration*, AIChE Journal, Oct. 1995, vol. 41, No. 10, at 2318.

M.A. O'Leary, D.A. Boas, B. Chance, and A.G. Yodh, *Experimental Images of Heterogeneous Turbid Media by Frequency-Domain Diffusing-Photon Tomography*, Optics Letters, Mar. 1995, vol. 20, No. 5, at 426.

Jozef Vavra, Antalik and Marek Liska, *Application of Regression Analysis in Spectroturbidity Size-Characterization Methods*, Part. Part. Syst. Charact. 12, 1995, 38-41.

Richard C. Haskell, Lars O. Svaasand, Tsong-Tseh Tsay, Ti-Chen Feng, Matthew S. McAdams and Bruce J. Tromberg, *Boundary Conditions for the Diffusion Equation in Radiative Transfer*, Journal of the Optical Society of America, Oct. 1994, vol. 11, No. 10, at 2727.

Nai-ning Wang, Gang Zheng, and Xiao-shu cai, *A Theoretical and Experimental Study of the Total Light Scattering Technique for Particle Size Analysis*, Part. Part. Syst. Charact. 11, Feb. 1994, at 309-314.

John Dimitratos, Guillermo Elicabe, and Christos Georgakis, *Control of Emulsion Polymerization Reactors*, AIChE Journal, Dec. 1994, vol. 40, No. 12, at 1993.

Ronald G. Sparks and Charles L. Dobbs, *The Use of Laser Backscatter Instrumentation for the On-Line Measurement of the Particle Size Distribution of Emulsions*, Part. Part. Syst. Charact. 10, Jul. 1993, at 279-289.

James R. Rawlings, Stephen M. Miller, and Walter R. Witkowski, *Model Indentification and Control of Solution Crystallization Processes: A Review*, Ind. Eng. Chem. Res., 1993, vol. 32, No. 7, at 1276.

D. Jeffrey Lischer and Michael Y. Louge, *Optical Fiber Measurements of Particle Concentration in Dense Suspensions: Calibration and Simulation*, Applied Optics, Aug. 1992, vol. 31, No. 24, at 5106.

Graaff, J.G. Aarnoudse, Jr. Zijp, P.M.A. Sloot, F.F.M. Mul, J. Greve, and M.H. Koelink, *Reduced Light-Scattering Properties for Mixtures of Spherical Particles: A Simple Approximation Derived from Mie Calculations*, Applied Optics, Apr. 1992, vol. 31, No. 10, at 1370.

H. Garcia-Kubio, *Refractive Index Effects on the Absorption Spectra of Macromolecules.* Macromolecules, 1992, at 2608.

Guillermo E. Elicabe and Luis H. Garcia-Rubio, *Latex Particle Size Distribution from Turbidimetric Measurements*, Polymer Characterization, 1990, at 84.

Jager, H.J.M. Kramer, E.J. De Jong, *On-Line Particle Size Measurement in Dense Slurries*, Powder Technology, 1990. at 155-162.

Seth Fraden and Georg Maret, *Multiple Light Scattering from Concenrated, Interacting Suspensions*, Physical Review Letters, Jul. 1990, vol. 65, No. 4, at 512.

John C. Thomas and Victoria Dimonie, *Fiber Optic Dynamic Light Scattering from Concentrated Dispersion, 3: Particle Sizing in Concentrates*, Applied Optics, Dec. 1990, vol. 29, No. 36, at 5332.

Joseph Pierce, Dilip Paithankar, Christina Hutchinson, David Taylor and Eva Sevick-Muraca, *Particle Size Measurement in Suspensions through Frequency-Domain Photon Migration Measurements*, Presentatioin to Fine Particle Society Meeting of Aug. 25, 1995.

Michael S. Patterson, Steen J. Madsen, J. David Moulton and Brian C. Wilson, *Diffusion Equation Representation of Photon Migration in Tissue* (date unknown).

Akira Ishimaru, Robert J. Marks, II, Leung Tsang, Chi M. Lam, and Dong C. Park, *Optical Sensing of Particle Size Distribution by Neural Network Technique* (date unknown).

Eva M. Sevick-Muraca and Kavi Sharma, *Measurements of Photon Migration for Particle Sizing in Optically Dense Suspensions*, AIChE Journal, Nov. 1994.

Dilip Paithankar, Jeff Kao, and Eva Sevick-Muraca, *Particle Size Distribution Estimation via Solution of the Inverse Problem of Multi-Wavelength Scattering Coefficient Measurements*, Chem. Eng. Prog., Aug. 1995.

Patterson, M.S. J.D. Moulton, B.C. Wilson, and B. Chance, *Applications of time-resolved Light Scattering Measurements using Phase Modulation Spectroscopy*, Proc. SPIE, Int. Soc., Opt. Eng., 1203, 62 (1991).

Eva M. Sevick-Muraca and Dilip Paithankar, *Process Monitoring: Photon Migration Measurements in Particle Systems, Fine Particle Society Meeting*, Aug. 1995.

M.A. O'Leary, E.A. Boas, X.D. Li, B. Chance, and A.G. Yodh., "*Fluorescence Lifetime Imaging in Turbid Media*," Optics Letters, vol. 21, No. 2, pp. 158-160,) Jan. 15, 1996.

\* cited by examiner

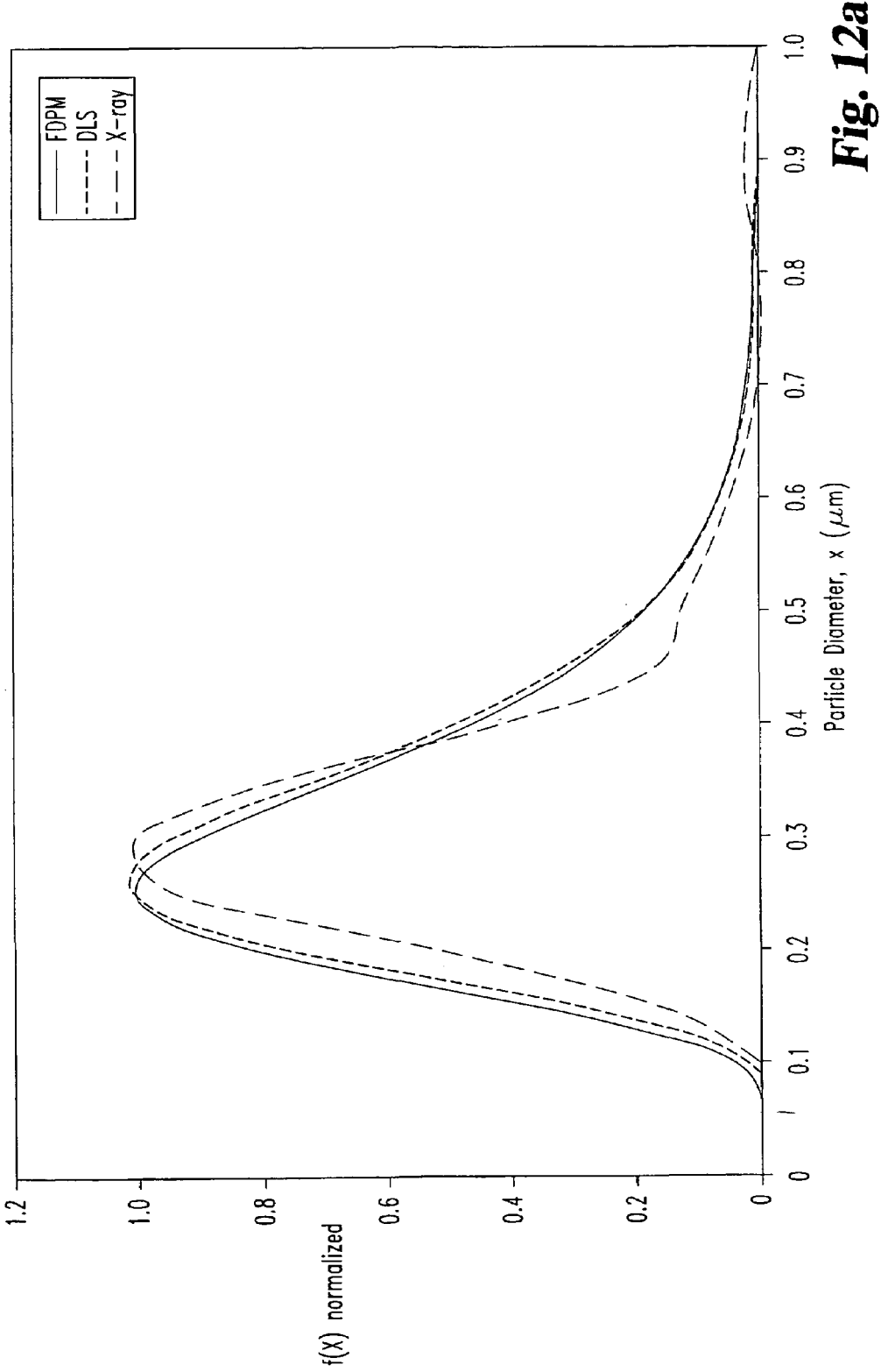

PARTICLE ANALYSIS SYSTEM AND METHOD

CROSS-REFERENCES

This application is a continuation-in-part of U.S. patent application Ser. No. 08/747,112, filed 8 Nov. 1996 now U.S. Pat. No. 5,818,583 and claims the benefit of U.S. Provisional Application No. 60/050,809, filed 26 Jun. 1997.

GOVERNMENT RIGHTS IN THE INVENTION

The U.S. Government has a paid-up license in this invention and the right in limited circumstances to require the patent owner to license others on reasonable terms as provided by the terms of the National Science Foundation Young Investigator Award No. BES-9496239 and the National Institutes of Health Research Center Development Award K04-CA68374.

BACKGROUND OF THE INVENTION

The present invention relates to the analysis of particles with multiply scattered light, and more particularly, but not exclusively, relates to the determination of size distribution and volume fraction of particles using photon migration techniques.

Today's chemical industry heavily relies on particulate or dispersed phase processes. The quality of many industrial products produced by these processes relates to the size distribution of the particles in terms of diameter or another designated dimension. For example, Particle Size Distribution (PSD) is highly relevant to the application, texture, and appearance of titanium dioxide based paint products. In addition, emulsion polymerization processes produce paints, various coatings, and synthetic rubbers to name only a few. Since emulsion polymerization involves the growth of suspended polymer particles. PSD measurements can yield insight into the extent of reaction and molecular weight distribution and can also provide means for product characterization. These measurements can also be adapted to many crystallization processes, such as in the food industry, pharmaceutics, agricultural products, and bulk chemicals. One way to optimize many of the processes involving a dispersion of particles is by providing on-line measurement of particle size distribution in combination with robust process control responsive to these measurements. Rawlings, J. B., Miller, S. M., and W. R. Witkowski, *Model Identification and Control of Solution Crystallization Processes*, Ind. Eng. Chem. Res., 32, 1275–1296 (1993); Farrell, R. J. and Y -C. Tsai, *Nonlinear Controller for Batch Crystallization: Development and Experimental Demonstration*, AlChE J., 41, 2318–2321 (1995); and Dimitratos, J., Elicabe, G., and C. Georgakis, *Control of Emulsion Polymerization Reactors*, AlChE J., 40, 1993–2021 (1994) are cited as additional sources of background information concerning chemical process control.

Despite the usefulness of PSD information, technology has not advanced such that these measurements can be made consistently under a wide variety of conditions and in a cost-effective manner. Moreover, the ability to determine PSD and the volume occupied by the dispersed particles (the "volume fraction") through "on-line" observation of the particles as they participate in the process remains elusive. These limitations adversely impact the development of optimal process controls for batch, semi-batch, and continuous reactors. The absence of this on-line measurement capability also impedes accurate model verification important in the formulation of a control model for non-linear processes. Typically, the lack of accurate modeling coupled with the lack of robust measurements have forced the use of open-loop control based upon less efficient downstream measurements; adversely impacting quality and efficiency.

Several laboratory particle sizing techniques exist, such as size-exclusion chromatography, capillary hydrodynamic fractionation, and photosedimentation; however, these techniques cannot provide on-line information about the process. Similarly, several optical techniques have been developed to provide PSD information. One of these techniques involves turbidity measurements which monitor the attenuation of light at multiple wavelengths traveling through a sample along a straight line path (180° relative to the incident light). Because these measurements do not account for backscatter nor multiple scattering of light back into the path length, turbidity analysis is only effective for diluted samples such that the product of turbidity, $\tau$, and pathlength, L, is less than about 0.3. In other words, the optical path of the sample is no less than about three times the mean distance between scattering particles. Van de Hulst, H. *Light Scattering by Small Particles* Dover Publications, New York (1983); J. Wang, and F. R. Hallet, *Spherical Particle Size Determination by Analytical Inversion of the UV-Visible-NIR Extinction Spectrum*, Appl. Optics, 35, 193–200 (1996); and J. Vavra, Antalik, J., and M. Liska, *Application of Regression Analysis in Spectroturbidity Size Characterization Methods*, Part. Part. Syst. Charact. 12, 38–41 (1995) are cited as sources of additional information concerning turbidity based systems.

Another optical approach is Dynamic Light Scattering (DLS), also termed quasi-elastic light scattering or photon correlation spectroscopy. DLS systems monitor the fluctuation of light intensity due to the Brownian motion of a single particle into and out of the near-field. From the time-dependence of intensity fluctuations, the particle diffusion coefficient can be computed and the radius obtained from the Stokes-Einstein equation. A statistical number of measurements of diluted and pretreated samples can provide a PSD. Notably, DLS techniques are often used as the laboratory "standard" for spherical particles having a diameter of less than 10 microns. Thomas, J. C. and V. Dimonie, *Fiber Optic Dynamic Light Scattering from Concentrated Dispersions. 3: Particle Sizing in Concentrates*, Appl. Optics., 29, 5332–5335 (1990), and U.S. Pat. Nos. 5,502,561 and 4,781, 460 are cited as sources of additional background information concerning DLS techniques.

In still another approach, angular light scattering or "diffraction" measurements are employed which monitor the angular scatter of light at a single wavelength due to diffraction from a single particle. Using classical scattering theory and known refractive indices of fluid and particle, an equivalent radius can be computed from an inverse solution. Again, a statistical number of measurements can provide PSD's from diluted samples of particles.

Turbidity, DLS, and diffraction measurements all require careful calibration of the light source and detector to provide meaningful measurements. Also, the possibility that wavelength dependent sample absorbance will vary during normal process disturbances and feedstock changes threatens the accuracy of these techniques. More importantly, these approaches all require a relatively dilute sample compared to the usual process concentration in order to be effective.

Turbidity, DLS, and diffraction techniques suffer from other limitations which complicates on-line implementation. For example, on-line application of these techniques would require automated sampling procedures. For sizing solids, side stream measurements frequently create maintenance problems such as clogged pumps, conduits and filters within sampling devices. For sizing of liquid droplets, side stream measurements often induce coalescence and breakup. Furthermore the mechanical action of most automated sampling procedures may change the particle, crystal, or dispersed phase size distribution. Moreover, on-line measurements under these approaches may require substantial dilution, phase separation, or sample destruction to be effective.

One system which attempts to solve these problems is a laser reflection or "backscatter" technique, such as the PAR TEC 100 available from Laser Sensor Technology. This system includes a laser with a narrow beam focused directly into a polydisperse medium undergoing processing. The focal position is made to vibrate at a high rate so that the beam travels significantly faster than particles in the medium. In theory, particles intercept the beam and reflect light for a duration of time which is proportional to the particle size. The reflected light is detected and timed, and a particle size is inferred from this information. To reconstruct a size distribution, the instrument counts the number of times each size occurs. Besides the constraint on speed of the beam relative to particle motion, tests have shown that this system consistently measures small particles as too large and large particles as too small. Also, the range swept by the laser beam must be smaller than the smallest particle size to be measured.

Similar to DLS and diffraction measurements, laser reflection techniques are based upon discrete single particle measurements to reconstruct PSD. Laser reflection measurements are sensitive to erroneous positioning of the focal plane, contribution of higher order scattering, and sampling error brought about by the hydrodynamic partitioning of large particles away from the wall and sensor head. In addition, the measurements are reported not to be accurate with non-opaque particles or dispersed droplets. Sparks, R. G., and C. L. Dobbs, *The Use of Laser Backscatter Instrumentation for On-Line Measurement of the Particle Size Distribution of Emulsions*, Part. Part. Syst. Charact. 10, 279–289 (1993) provides additional information concerning this technique.

Turbidity, DLS, Diffraction, and Laser reflection are all limited to some extent by the multiple scattering of light by the particles. These systems attempt to confine this problem by sampling and dilution, or by adjusting various other system parameters. Also hampering the effectiveness of these techniques is the need to calibrate the equipment in situ. Process upsets, feedstock changes, or even normal batch process changes may invalidate the calibration. Depending upon the application, the sensor output for feedback control could be catastrophic absent proper calibration.

Thus, a need remains for a technique to analyze particles in a process stream which is self-calibrating and interrogates the process stream without requiring sampling or dilution. Preferably, this technique may be used to determine particle size distribution and volume fraction regardless of particle concentration level.

SUMMARY OF THE INVENTION

The invention relates to analysis of particles using photon migration techniques. Several aspects of the invention are novel, non-obvious, and provide various advantages. While the actual nature of the invention covered herein can only be determined with reference to the claims appended hereto, certain features which are characteristic of the present invention are described briefly as follows.

In one form of the present invention, particle size distribution or volume fraction of a number of particles in suspension is determined from the measurement of one or more propagation characteristics of multiply scattered light re-emitted from the suspension. As used herein, "particles" include crystals, solids, liquid droplets, microbes, or microbe organelles. Also, as used herein, "multiple scattering" of light refers to the condition where, at a given wavelength, a photon is more likely to be consecutively scattered many times between particles due to a refractive index mismatch between the dispersed particles and the host medium before being absorbed or detected. Generally, the multiple scattering condition entails that the particles be close enough to one another so that the distance a photon travels between scattering events is much smaller than the length traveled before absorption. Thus, multiple scattering of light occurs when $\mu_s' \gg \mu_a$, where the absorption coefficient, $\mu_a$, indicates the ability of a substance to absorb light of a particular wavelength, and the isotropic scattering coefficient, $(1-g)\mu_s = \mu_s'$, indicates the ability of a substance to scatter light of a particular wavelength in any particular direction. Preferably $\mu_s'$ is at least 10 times greater than $\mu_a$. More preferably, $\mu_s'$ is at least 100 times greater than $\mu_a$. Also, as used herein "multiply scattered light" refers to light that has traveled at least 5 times the mean isotropic scattering length for a particular wavelength, defined as $1/\mu_s'$.

When light is multiply scattered by particles in a fluid, it typically travels a greater distance and therefore has a longer travel time as compared to a direct path through the fluid without encountering the particles. The "time of flight" of photons through a scattering media is on the order of about 1 nanosecond. Because many different scattering paths are likely, time of flight is usually characterized as a distribution; however, this distribution typically varies with the light wavelength, the refractive character of the particles relative to the media, the size of the particles, and the volume fraction of the particles. Thus, in a further form of the present invention, measurements corresponding to photon migration time or travel time through the scattering media may be obtained and utilized to characterize the particles.

At high particle concentrations, interactions between particles have a substantial influence on the light scattering properties of a multiple scattering media. This influence may degrade measurements which fail to account for particle-to-particle interactions. To adjust for particle interactions, a particle interaction parameter, which varies with particle concentration, may be utilized. In one form of the present invention, a particle structure factor is utilized, such as the Percus-Yevick model, which further provides an assessment of the stability of a corresponding particle suspension.

In another form, particles suspended in a medium are exposed to a number of light wavelengths each being intensity-modulated at a predetermined frequency. Multiply scattered light from the medium in response to this exposure is detected to characterize propagation of the multiply scattered light through the medium with a number of values. The values each correspond to a different one of the wavelengths and are each representative of at least one of a phase or an amplitude of the multiply scattered light relative to the predetermined frequency. An output is provided that is determined from the values. The output corresponds to at least one of particle size distribution, volume fraction, or a particle interaction parameter. This particle interaction parameter corresponds to a nonlinear relationship between particle concentration and an isotropic scattering coefficient for the particles.

In an additional form, a number of particles suspended in a medium are exposed to a number of light wavelengths of predetermined time-varying intensity. Multiply scattered light form the particles in response to this exposure is detected to determine a number of values each corresponding to a different one of the wavelengths. These values are each representative of a time of flight characteristic of the particles. The output corresponds to at least one of particle size distribution, volume fraction, or a particle interaction parameter. This particle interaction parameter corresponds to a nonlinear relationship between particle concentration and an isotropic scattering coefficient for the particles.

In a further form, particles are exposed to an incident light with a predetermined time-varying intensity. The particles are sufficiently close to each other to multiply scatter light. Multiply scattered light is detected from the particles in response to the incident light to determine a first value corresponding to an observed isotropic scattering coefficient of the particles. An estimate corresponding to at least one of volume fraction or size distribution of the particles is established, and a second value is calculated as a function of the estimate. The second value corresponds to a calculated isotropic scattering coefficient. The first and second values are compared to establish an error, and the estimate is changed. The calculation of the second value, comparison of the first and second values, and changing of the estimate is repeated until the error reaches a desired minimum.

In still another form of the present invention, a method of analysis includes exposing a fluid with a number of suspended particles to an incident light. The particles are sufficiently concentrated in the fluid to scatter light. Multiply scattered light in response to this exposure is detected to determine a time-based value characteristic of propagation time of the multiply scattered light through the fluid. A quantity is determined as a function of the value which corresponds to an isotropic scattering coefficient of the fluid. An output is provided that corresponds to at least one of particle volume fraction, particle size distribution, or a particle interaction parameter corresponding to particle-to-particle interactions that influence light scattering behavior of the particles. The output is determined from the quantity.

A further form of the present invention is a system for analyzing a number of particles suspended in a medium in sufficient concentration to multiply scatter light. This system includes a light source configured to expose the medium to a number of different predetermined wavelengths of incident light each having a predetermined time-varying intensity and a sensor spaced apart from the source. The sensor is configured to provide a detection signal corresponding to detected light. This detected light originates from the source and is multiply scattered by the particles. The system also includes a processor responsive to the first detection signal. The processor receives an exposure signal corresponding to the incident light and generates propagation signals by comparing the detection signal and the exposure signal for each of the wavelengths. These propagation signals characterize time of flight of the detected light through the medium resulting from multiple scattering by the particles. The processor is also configured to generate scattering signals corresponding to an isotropic scattering coefficient of the medium. The scattering signals are correspondingly determined from the propagation signals. The processor further generates an output signal indicative of one of size distribution or volume fraction of the particles which is determined from the scattering signals and a structure factor. This structure factor accounts for particle-to-particle interactions that influence light scattering behavior of the particles. The system further includes an output device responsive to the output signal to provide an output corresponding to the size distribution or volume fraction of the particles.

Yet another form of the present invention is a system for analyzing a number of particles suspended in a medium in sufficient concentration to multiply scatter light. This system includes a light source, a sensor spaced apart from the light source, a processor, and an output device. The sensor provides a detected light signal corresponding to multiply scattered light from the particles at different wavelengths in response to exposure to the source. The processor is responsive to the emission signal and includes a calculation means for generating an output signal corresponding to at least one of a size distribution, volume fraction, or a structure factor of the particles in accordance with an observed isotropic scattering coefficient of the medium. The processor determines a value representative of the observed isotropic scattering coefficient from the detected light signal. The output device responds to the output signal to provide an output corresponding to at least one of the size distribution, the volume fraction, or the structure factor of the particles.

Accordingly, one object of the present invention is to determine particle size distribution, particle volume fraction, or a particle interaction parameter from multiply scattered light.

Another object of the present invention is to provide a self-calibrating system for the on-line determination of particle size distribution and volume fraction by detecting the propagation characteristics of multiply scattered light from particles dispersed in a fluid medium.

Yet another object is to determine one or more optical coefficients of a number of particles suspended in a medium by sensing propagation characteristics of multiply scattered light from the particles and to provide a size distribution or volume fraction of the particles from one or more optical coefficients.

Still another object of the present invention is to provide an estimation algorithm to inversely solve for size distribution, volume fraction, or structure factor of a number of particles using observed values representative of the isotropic scattering coefficient of the particles at different wavelengths. This estimation may be based on an expected form of the distribution. Also, the estimation may account for mass of the particles.

An additional object of the present invention is to provide a technique for determining a particle interaction parameter which accounts for particle-to-particle interactions that vary with particle concentration and influence light scattering by the particles.

Further objects, advantages, features, forms, and aspects of the present invention will become apparent from the drawings and description contained herein.

BRIEF DESCRIPTION OF THE DRAWINGS

FIGS. 12*a*–12*b* are graphs depicting size distributions for aqueous dispersions of $TiO_2$ particles supplied as suspension samples S1 and S2, respectively, which compare measurement of size distribution in accordance with the present invention to measurements by Dynamic Light Scattering (DLS) and X-ray scattering techniques.

DESCRIPTION OF PREFERRED EMBODIMENTS

Figure 1:
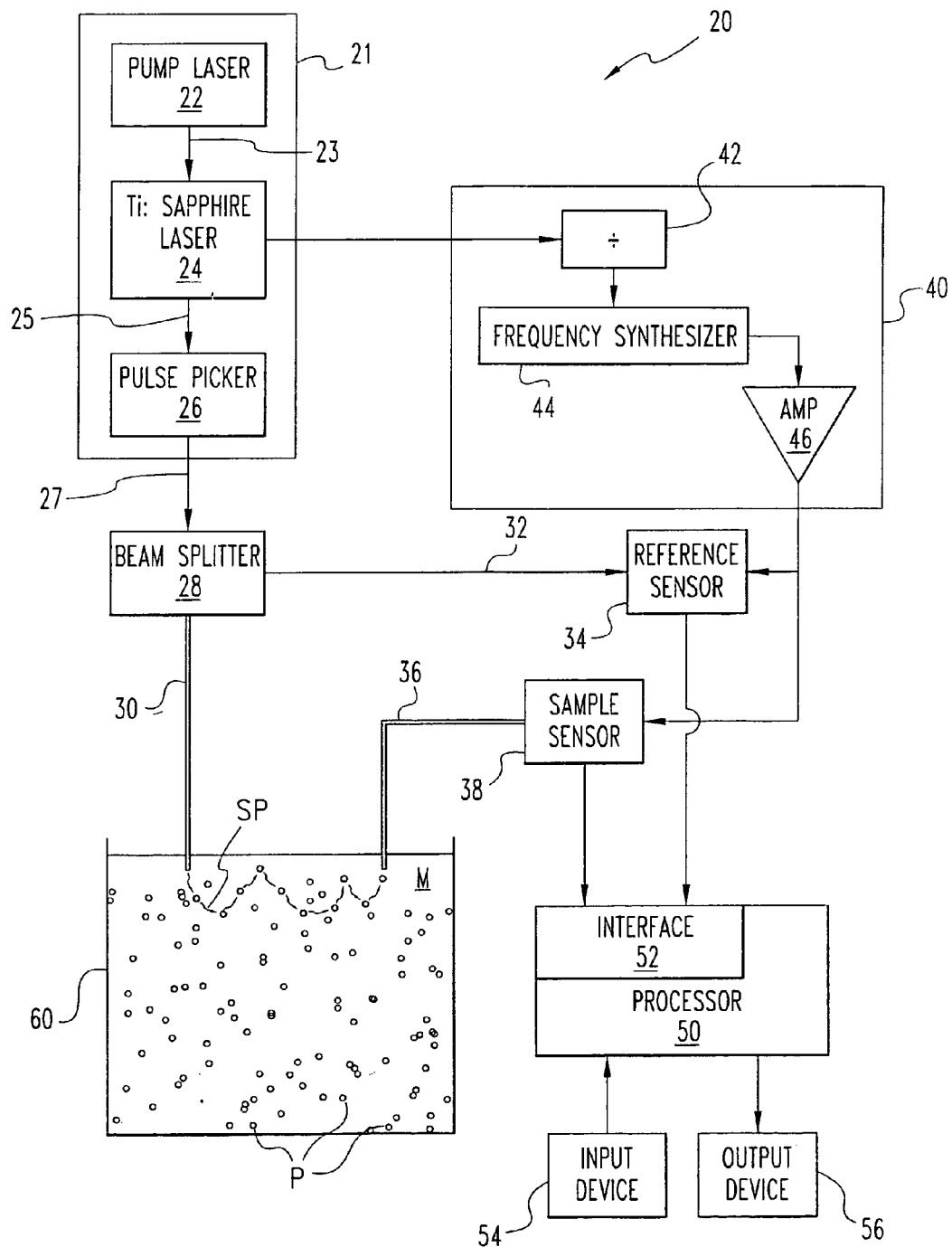
FIG. 1 is a schematic view of an analysis system of one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described techniques, systems, and devices, and any further applications of the principles of the invention as described herein are contemplated as would normally occur to one skilled in the art to which the invention relates.

FIG. 1 depicts an analysis system 20 of one embodiment of the present invention. System 20 includes a light source 21 which includes Argon ion laser 22, Titanium:Sapphire laser 24, and pulse conditioner 26. Laser 22 generates a monochromatic output beam 23 using electrical discharges in a conventional manner. In one preferred embodiment, laser 22 is provided by a Beam-Lok model 2060 laser available from Spectra Physics, CA which is configured to deliver a beam with a diameter of less than 2 millimeters (mm) at a wavelength of 514.5 nanometers (nm). A constant output power of the Beam-Lok model 2060 laser is selected from a range of 0 and 10 watts (W) for this embodiment.

Beam 23 from laser 22 is configured to "pump" laser 24 using conventional techniques. In one embodiment, source 21 includes a Tsunami Ti:Sapphire laser, model 3950B, available from Spectra Physics, Mountain View, Calif. for laser 24 and the Beam-Lok model 2060 for laser 22. Beam 23 is directed into a cavity of laser 24 to impinge upon a titanium-doped sapphire rod and excite titanium ions of the rod. In response, a monochromatic, unidirectional optical pulse train of light pulses is produced which is designated beam 25. Preferably, beam 25 has generally equally spaced light pulses of 2 picoseconds (psec) Full Width Half Maximum (FWHM) at a repetition rate of about 80 Megahertz (MHz). The output power of beam 25 is preferably maintained at about 20% of the input power of beam 23.

Beam 25 is directed to pulse picker 26. Picker 26 provides two functional capabilities: (1) to select an output pulse frequency less than or equal to the pulse repetition rate of pulses from input beam 25 and (2) to selectively halve the wavelength (λ) of the input beam. The frequency selection capability is provided by directing beam 25 to an Acousto-Optic Modulator (AOM) crystal. The AOM crystal controllably diffracts pulses from the impinging beam 25 at an angle relative to the main beam in accordance with a electromagnetic Radio Frequency (RF) input. The rate of diffracted or is "picked" pulses may be selected to provide a number of different output repetition rates less than or equal to the input frequency.

Picker 26 also includes a Second Harmonic Generation (SHG) crystal to selectively produce output wavelengths at one half the input wavelength λ. Picker 26 is configured so that beam 25 passes through the SHG crystal after the AOM crystal. The SHG crystal emits a single photon for every two photons absorbed. The energy level of the emitted photon is approximately double the energy of each of the two absorbed photons. As a result, the wavelength corresponding to the emitted photon is about one half and the frequency is about doubled compared to each of the two input photons. The λ and 0.5λ outputs are separated by a prism to provide two outputs collectively represented as beam 27. The λ output is selected for wavelengths in the 720 to 900 nm range, and the 0.5λ output is selected for wavelengths in the 360 to 450 nm range.

Beam 27 from source 21 is directed to a glass slide beam splitter 28 which splits beam 27 to direct about 80% along optical fiber 30 and the remaining 20% along fiber 32 to reference sensor 34. Light directed along fiber 30 enters sample tank 60 to encounter particles P suspended in fluid medium M. Particles P are sufficiently concentrated in medium M to multiply scatter light pulses entering by fiber 30. This multiple scattering is diagrammatically represented by scattering path SP. Multiply scattered light is collected by fiber 36, and is then directed to sample sensor 38. Preferably, sensors 34, 38 are Photomultiplier Tubes (PMTs), (Hamamatsu R928, Hamamatsu, Japan) and fibers 30, 32, 36 are 1000 mm optical fibers (HCP-M1000T-08, Spectran, Avon, Conn.); however, in other embodiments other sensor types and couplings are envisioned as would occur to one skilled in the art.

Sensors 34, 38 are operatively coupled to heterodyne subsystem 40 and processor 50 via interface 52. It should be appreciated that the light pulse train incident on sensors 34 and 38 may be described in terms of a number of intensity modulated frequencies which are multiples of the pulse repetition rate via Fourier analysis. Heterodyne subsystem 40 and processor 50 provide frequency domain information about light collected from sensors 34, 38 in terms of one or more of the intensity modulation frequencies.

Where the source 21 pulse repetition rate is $\omega$ and q is a whole number multiplier, heterodyne subsystem 40 gain modulates sensors 34, 38 at a harmonic $q\omega$ plus a cross-correlation frequency offset, $\Delta\omega$, using conventional techniques. For one embodiment, an RF signal from frequency synthesizer 44 (Marconi Instruments Signal Generator, model 2022A) is phase-locked to the pulse frequency of source 21 via divider 42 and outputs the gain modulation frequency of $q\omega+\Delta\omega$ for amplification by power amp 46 (model 1403LA, ENI, Rochester, N.Y.). The output of power amp 46 modulates the signals from sensors 34, 38 resulting in a signal of frequency $\Delta\omega$ from each sensor 34, 38. Comparative frequency domain information, including phase-shift ($\theta$) and relative magnitude (M) (also called demodulation amplitude) for harmonic frequency $q\omega$ of the pulsed laser light delivered to sensors 34, 38 is obtained by comparing these outputs. By changing q, measurement of phase shift ($\theta$) and relative magnitude (M) may be obtained as a function of modulation frequency. Furthermore, by varying the wavelength ($\lambda$) of the output from source 21, the phase shift ($\theta$) and relative magnitude (M) may be obtained as a function of $\lambda$.

In one embodiment, the source 21 pulse repetition rate is 80 MHz which is divided by 8 by divider 42 and input to synthesizer 44 to provide the phase-locked loop. A 4 MHz pulse train is selected with picker 26 and the corresponding cross-correlation offset frequency is 100 Hz. Synthesizer 44 is preferably a Marconi Instruments signal generator, model 2022A, and amplifier 46 is a model 1403LA available from ENI, Rochester, N.Y. Preferably, interface 152 is a conventional data acquisition module suitable to digitize the output of sensors 34, 38 for subsequent analysis by processor 50. Processor 50 may be an electronic circuit comprised of one or more components. Similarly, processor 50 may be comprised of digital circuitry, analog circuitry, or both. Also, processor 50 may be programmable, an integrated state machine, or a hybrid combination thereof. Preferably, processor 50 is comprised of one or more devices of the a digitally programmable variety.

Processor 50 is coupled to at least one input device 54 and at least one output device 56. Preferably, input device 54 is a keyboard or input control of a conventional variety, and output device 56 is a Cathode Ray Tube (CRT) based video display, printer, or other image display system known to those skilled in the art. System 20 is well-suited to conveniently deliver and detect light pulses at a selected rate and wavelength in a laboratory setting. In other embodiments, the configuration of system 20 may vary to provide and sense light at selected wavelengths and with a desired time-varying intensity using techniques known to those skilled in the art.

Figure 2:
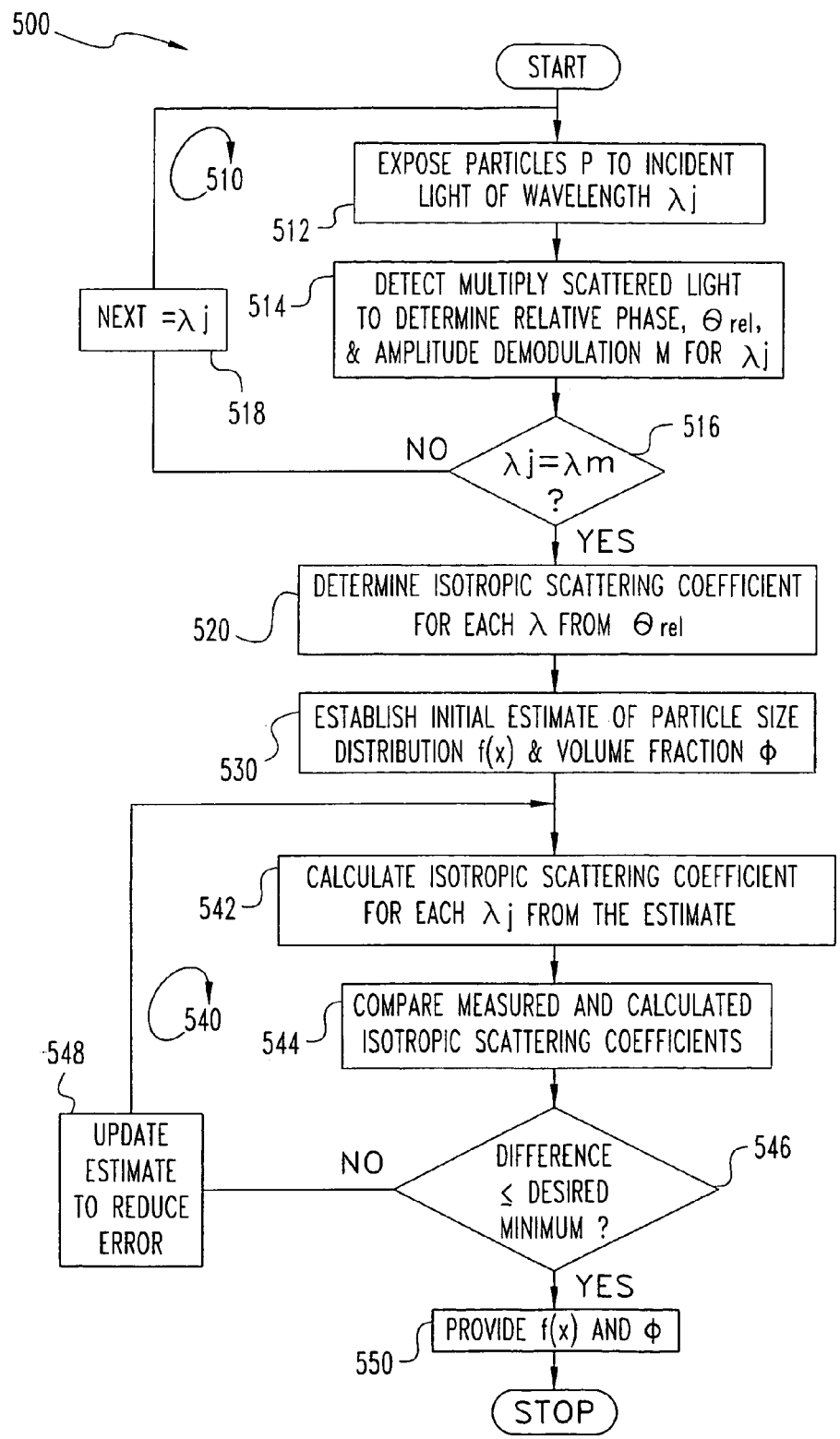
FIG. 2 is a flow chart illustrating one process of the present invention performed by the system of FIG. 1.

FIG. 2 is a flow chart depicting process 500 which is performed using system 20. Preferably, processor 50 is configured to execute a program that performs at least the more calculation intensive aspects of process 500. With regard to these calculations, selected variables employed in the description of process 500 are presented as follows in Table 1:

TABLE 1

Description of Selected Variables

| | GENERAL VARIABLES |
|---|---|
| a,b,c,d | parameters governing the size distribution and volume fraction for inverse solution. |
| k | wavelength number, $k = 2\pi/\lambda$ [nm$^{-1}$] |
| $c_n$ | speed of light through random medium, [cm/sec]. |
| D | optical diffusion coefficient [cm]. |
| f(x) | particle size distribution (volume distribution) [dimensionless]. |
| g | mean cosine of angular scatter. |
| r | radius of particle, [microns]. |
| x | diameter of particle, [microns]. |
| m | depth of sinusoidal intensity modulated light. |
| M | amplitude modulation of re-emitted, multiply scattered light. |
| n | relative refractive index of particle. |
| N | number of Jacobian Matrix bins. |
| ND | number density of particles in suspension |
| N* | number of particle sizes for discrete filter application. |
| q | positive integer frequency multiple. |
| q | q is an intermediate variable, $q = [(4\pi n/\lambda)(\sin(\theta/2))]$. |
| $Q_{scat}$ | scattering efficiency of single scatterer. |
| $q_{scat}$ | angular scattering efficiency. |
| S(q) | structure factor. |
| z | number of discrete particle size increments. |
| $\alpha$ | regularization parameter. |
| $\chi^2$ | minimization function. |
| $\phi$ | dispersed phase or solids volume fraction. |
| $\Phi$ | photon fluence, equal to the local concentration of photons times the speed of light [photons/cm$^2$ sec]. |
| $\theta$ | phase-shift of amplitude modulated light relative to incident light, [degrees or radians]. |
| $\theta_{rel}$ | relative phase-shift between two different detectors at different positions [degrees or radians]. |
| $\lambda$ | wavelength of light. |
| $\mu_s$ | scattering coefficient, [cm$^{-1}$]. |
| $\mu_a$ | absorption coefficient, [cm$^{-1}$]. |
| $\mu_s' = (1-g)\mu_s$ | isotropic scattering coefficient [cm$^{-1}$]. |
| $\sigma$ | mean particle diameter. |
| $\omega$ | modulation frequency. |
| | SUPERSCRIPT VARIABLES |
| o | observed. |
| c | computed. |
| | SUBSCRIPT VARIABLES |
| h | index to Jacobian bins. |
| i | index to particle diameter. |
| j | index to wavelengths $\lambda$. |
| M | maximum number of wavelengths $\lambda$. |
| p | discrete low pass filter index. |
| | VECTOR AND MATRIX VARIABLES |
| I | identity matrix. |
| r | position vector. |
| $r_s$ | position vector of the source fiber 30, [cm]. |
| $r_d$ | position vector of the detector fiber 36, [cm]. |
| $\zeta$ | Matrix containing updates to size distribution and volume fraction. |
| $\xi$ | Discrete filter parameter. |
| $\Im$ | Jacobian matrix describing changes in isotropic scattering with size distribution and volume fraction. |

Referring to FIGS. 1 and 2, process 500 begins by entering loop 510 at stage 512. In stage 512, particles P in medium M are exposed to pulses of light of wavelength $\lambda_j$ from source 21 via fiber 30; where "j" is the wavelength index form j=1, M. The location of the source light is designated by position vector $r_s$. In stage 514, multiply scattered light resulting from the exposure in stage 512 is collected at detector location rd corresponding to the position of fiber 36. Frequency domain quantities relating to $\theta(r_d)$ and $M(r_d)$ are collected for the given $\lambda_j$ and stored by processor 50. In one embodiment, phase error inherent in the instrumentation of system 20 is reduced by collecting the multiply scattered light in two locations, $r_{d1}$ and $r_{d2}$, and determining $\theta_{rel}=|\theta(r_{d1})-\theta(r_{d2})|$ as more fully described in conjunction with stage 520.

Next, conditional 516 is encountered. Conditional 516 tests whether frequency domain information for all wavelengths of interest have been collected. If not, the next wavelength $\lambda_{j+1}$ is selected by appropriate adjustments to source 21 and control flows back to stage 512; closing loop 510. After frequency domain information for all desired wavelengths has been collected, then conditional 516 is satisfied and control flows to stage 520.

In stage 520, the isotropic scattering coefficient for each of the wavelengths $\lambda_j$ is determined. This determination is based on the diffusion equation model of light propagation. Under conditions of multiple scattering, the time-dependent light propagation can be accurately modeled by a diffusion equation written here in the frequency domain:

$$-D(\lambda)\nabla^2 \Phi(r,\omega) + \frac{i\omega}{c_n(\lambda)}\Phi(r,\omega) + \mu_a(\lambda)\Phi(r,\omega) = \delta(r-r_s)m \quad (1)$$

where $\Phi(r,\omega)$ is the fluence of photons at position r within a propagating "photon density wave" modulated at frequency, $\omega$; $c_n$ is the speed of light through the medium; m is the depth of sinusoidal modulation of the source located at position $r_s$; $\mu_a(\lambda)$ is the wavelength dependent absorption coefficient that is equal to $\Sigma\epsilon[C]$, the sum of the product of extinction coefficients, $\epsilon$, and concentration, [C], for all light absorbing constituents present; and $D(\lambda)$ is an "optical diffusion coefficient" which is given by:

$$D(\lambda) = \frac{1}{3[\mu_a(\lambda) + (1-g)\mu_s(\lambda)]}. \quad (2)$$

The following are cited as additional sources of information concerning these relationships. A. Ishimaru, *Wave Propagation and Scattering in Random Media*, Academic Press, New York (1976); S. Chandrasekhar, *Radiative Transfer*, Oxford University Press, New York (1960); and R. C. Haskell, Svaasand, L. O., Tsay, T -T, Feng, T -C., McAdams, M. S., and B. J. Tromberg, *Boundary Conditions for the Diffusion Equation in Radiative Transfer*, J. Opt. Soc. Am. A 11, 2727–2741 (1994).

The term $(1-g)\mu_s=\mu_s'$ is the isotropic scattering coefficient which arises from multiple scattering and is dependent upon the particle size distribution, f(x) (where x is the diameter of the particles), and the total volume fraction, $\phi$ as follows:

$$(1-g)\mu_s(\lambda) = \mu_s'(\lambda) = \int_0^\infty \frac{3Q_{scat}(x,n,\lambda)[1-g(x,n,\lambda)]}{2x}\phi f(x)dx \quad (3)$$

where g is the mean cosine of the scattering angle from a single particle and $Q_{scat}$ is the scattering efficiency. Both quantities are computed using classical Mie theory. See G. F. Bohren, and D. R. Hoffman, *Absorption and Scattering of Light by Small Particles*, John Wiley, New York (1983) for additional information concerning this computation.

The real and imaginary parts of $\Phi(r_s-r_d,\omega)$ can be used to predict the measured phase-shift, $\theta$, and amplitude modulation, M, measured at detector position, $r_d$:

$$\theta(r_d,\omega,\lambda) = \tan^{-1}\frac{Im\Phi(r_d,\omega,\lambda)}{Re\Phi(r_d,\omega,\lambda)} \quad (4)$$

and $$M(r_d,\omega,\lambda) = \sqrt{[Im\Phi(r_d,\omega,\lambda)]^2 + [Re\Phi(r_d,\omega,\lambda)]^2} \quad (5)$$

The solution to equation (1) can be obtained for reflectance or transillumination measurements on semi-infinite random media as well as for finite geometry's in which the source and detector are separated by distance $|r_s-r_d|$. For simplicity, an infinite geometry is assumed which results in the following approximation:

$$\theta(r_d,\omega,\lambda) \approx \quad (6)$$
$$-|r_s-r_d|\sqrt{\frac{3\mu_s'(\lambda)\{(\mu_a(\lambda)c_n)^2+\omega^2\}^{\frac{1}{2}}}{c_n}}\sin\left[\tan^{-1}\left\{\frac{\omega}{\mu_a(\lambda)c_n}\right\}\right]$$

Measurement of phase-shift usually includes a contribution due to the electronics and photodetection systems. Upon conducting a spatially resolved phase-shift measurement at two or more consecutive detector positions, $r_{d1}$, $r_{d2}$, instrument errors are accounted for. The relative phase, $\theta_{rel}$ can then be predicted from the following relationship:

$$\theta_{rel}(\lambda) = \quad (7)$$
$$|\theta(r_{d1})-\theta(r_{d2})| = |r_{d1}-r_{d2}|\left(\frac{c_n^2\mu_a^2(\lambda)+\omega^2}{c_n^2 D^2(\lambda)}\right)^{\frac{1}{4}}\sin\left[\frac{1}{2}\tan^{-1}\left(\frac{\omega}{c_n\mu_a(\lambda)}\right)\right]$$

Equations (6) and (7) may be expressed in terms of the absorption coefficient $\mu_a$ and isotropic scattering coefficient $\mu_s'=(1-g)\mu_s$ through the substitution of equation (2) for $D(\lambda)$. Therefore, given $\theta(r_d)$ or $\theta_{rel}=|\theta(r_{d1})-\theta(r_{d2})|$ from the execution of loop 510, equations (6) and (7) may be fit, respectively, for an observed absorption coefficient $\mu_a$ and isotropic scattering coefficient $\mu_s'$ by applying a Levenberg-Maraquardt non-linear least square regression of the type disclosed in Press et al., *Numerical Recipes: The Art of Scientific Computing* (Cambridge University Press 1992) to the data tabulated as a result of the execution of loop 510 for each of the wavelengths of interest. Preferably, processor 50 accumulates the frequency domain information in memory and is programmed to execute a Levenberg-Maraquardt non-linear least square regression algorithm to provide these optical coefficients. The resulting observed isotropic scattering coefficients for the wavelengths $\lambda_j$ are represented as $(\mu_{s'})_j^o$. Preferably, $(\mu_{s'})_j^o$ is obtained by applying equation (7) to $\theta_{rel}$ measurements in stage 520.

Unlike conventional PSD measurement systems, these frequency domain measurements offer the ability to monitor absorption and scattering properties in multiply scattering systems without the need for spectral calibration of lamps or detectors to an external standard. Also, because the absorption and isotropic scattering coefficients do not appear as a product in equation (7), regression of phase-shift data provides an efficient means of determining optical characteristics from measurements of multiply scattered light.

Once $(\mu_{S'})_j^o$ has been obtained in stage 520, stage 530 is encountered. Stage 530 initiates an algorithm to inversely solve equation (3) for the integrands f(x) and φ given $(\mu_{S'})_j^o$. This inverse solution starts by estimating the product φf(x) in stage 530. Once this product is known, f(x) and φ may be separated by the relation $$\int_0^\infty \phi f(x)\, dx = \phi. \qquad (?)$$

Next, iteration loop 540 is entered at stage 542. In stage 542, the isotropic scattering coefficients for each of the wavelengths of interest are calculated from equation (3) using the estimate of φf(x). For this calculation, equation (3) is approximated by the summation equation (8) as follows:

$$(\mu_s')_j^c = \sum_{i=1}^{Z} \frac{3}{2} \frac{Q_{scat}(\lambda_j, n, x_i)}{x_i}(1 - g(\lambda_j, n, x_i))\phi f(x)\Delta x_i. \qquad (8)$$

For equation (8), an expected range of particle diameter x from $x_{min}$ to $x_{max}$ is determined and incremented into k number of discrete sizes $x_i = x_{min} + (i-1)\Delta x$, where $\Delta x = (x_{max} - x_{min})/(z-1)$ for i=1 to z; and the terms $Q_{scat}(\lambda_j, n, x_i)$ and $g(\lambda_j, n, x_i)$ are determined from look-up tables based on $\lambda_j$, n, $x_i$. The resulting set of calculated isotropic scattering coefficients, $(\mu_{S'})_j^c$ are then compared to the observed isotropic scattering coefficients, $(\mu_{S'})_j^o$ in stage 544. This comparison is performed in accordance with:

$$\chi^2 = \sum_{j=1}^{M}[(\mu_s')_j^o - (\mu_s')_j^c]^2 \qquad (9)$$

where it is desired to minimize $\chi^2$ so that it is less than or equal to an established error amount. Conditional 546 tests whether this minimization has taken place. If the minimum has been reached, then control flows to stage 550 and the estimate is provided as the measured product φf(x). Subsequently, f(x) and φ may be separated by performing a summation approximation of $$\int_0^\infty \phi f(x)\, dx = \phi.$$

However, if conditional 546 is not satisfied, then control flows to stage 548 to improve the estimate of φf(x). One embodiment for rapidly converging to the desired minimum error is through application of a Jacobian matrix relationship. Specifically, the product φf(x) is divided into N number of bins representing φf(x)$_h$, where h=1 to N. In order to update φf(x)$_h$ in each bin, the Jacobian matrix which describes the sensitivity of the isotropic scattering coefficient to changes in φf(x)$_h$ in each bin h and at each wavelength $\lambda_j$ is computed. This Jacobian matrix is given by:

$$\Im = \begin{bmatrix} \frac{\partial(\mu_s')_{\lambda_1}^c}{\partial(\phi f(x))_1} & \frac{\partial(\mu_s')_{\lambda_1}^c}{\partial(\phi f(x))_2} & \cdots & \frac{\partial(\mu_s')_{\lambda_1}^c}{\partial(\phi f(x))_N} \\ \frac{\partial(\mu_s')_{\lambda_1}^c}{\partial(\phi f(x))_1} & \frac{\partial(\mu_s')_{\lambda_1}^c}{\partial(\phi f(x))_2} & \cdots & \frac{\partial(\mu_s')_{\lambda_1}^c}{\partial(\phi f(x))_N} \\ \vdots & \vdots & \ddots & \vdots \\ \frac{\partial(\mu_s')_{\lambda_1}^c}{\partial(\phi f(x))_1} & \frac{\partial(\mu_s')_{\lambda_1}^c}{\partial(\phi f(x))_2} & \cdots & \frac{\partial(\mu_s')_{\lambda_1}^c}{\partial(\phi f(x))_N} \end{bmatrix} \qquad (10)$$

and each element is computed through a summation approximation of equation (3) with φf(x)$_h$ and φf(x)$_h$+Δφf(x)$_h$. The updates, δφf(x)$_h$, resulting from the differences between measured and computed isotropic scattering coefficients, can then be obtained from:

$$\Im^T \Im \Delta\zeta = \Im^T[(\mu_s')^o - (\mu_s')^c] \qquad (11)$$

which results in a system of linear equations that may be solved using Newton's method to obtain the vector Δζ containing the update values of φf(x) across all bins, h=1, N as follows:

$$\Delta\zeta = (\delta(\phi f(x))_1, \delta(\phi f(x))_2, \ldots \delta(\phi f(x))_N)^T \qquad (12)$$

The vectors, $(\mu_s')^o$ and $(\mu_s')^c$ contain the observed and computed values of isotropic scattering coefficients at the wavelengths of interest, j=1,M are:

$$(\mu_s')^o = ((\mu_s')_{\lambda_1}^o, (\mu_s')_{\lambda_2}^o, \ldots (\mu_s')_{\lambda_M}^o),\ (\mu_s')^c = ((\mu_s')_{\lambda_1}^c, (\mu_s')_{\lambda_2}^c, \ldots (\mu_s')_{\lambda_M}^c) \qquad (13)$$

The matrix $\Im^T\Im$ in equation (11) is sometimes ill-conditioned and may be more readily solved through regularization of the decomposition of $\Im^T\Im$. One type of regularization scheme is the Maraquardt-type which may be stated as:

$$(\Im^T\Im + \alpha I)\Delta\zeta = \Im^T[(\mu_s')^o - (\mu_s')^c] \qquad (14)$$

where I is the identity matrix and α may be a scalar or a diagonal matrix. By adding a contribution to the diagonal terms in equation (14), we make $\Im^T\Im$ more diagonally dominant which improves its invertability. The parameter α is usually determined by trial and error. Jiang, H., Paulsen, K., Osterberg, U., Pogue, B. and M. Patterson, *Optical image reconstruction using frequency-domain data: simulations and experiments*, J. Opt. Soc. Am. A 13, 253–266 (1996) is cited as a source of additional information concerning these calculations.

Once the estimate is updated in stage 548, control returns to stage 542, via loop 540 to calculate the isotropic scattering coefficients based on the updated estimate. Repeated executions of loop 540 are anticipated before the desired minimum value of $\chi^2$ is obtained.

Preferably, stages and conditionals corresponding to reference numbers 520 to 550 are performed through a software routine executed by processor 50, and processor 50 is of a type suitable to perform the extensive calculations of process 500 in an adequate amount of time. Notably, the phase shift may be determined from detection at a single location $r_d$ using equation (6) or at multiple locations to determine the $\theta_{rel}$ as a function of $r_{d1}$ and $r_{d2}$ using equation (7). Furthermore, instead of phase shift, process 500 may be adapted to determine f(x) and φ based on amplitude M measurements in the frequency domain.

Figure 2A:
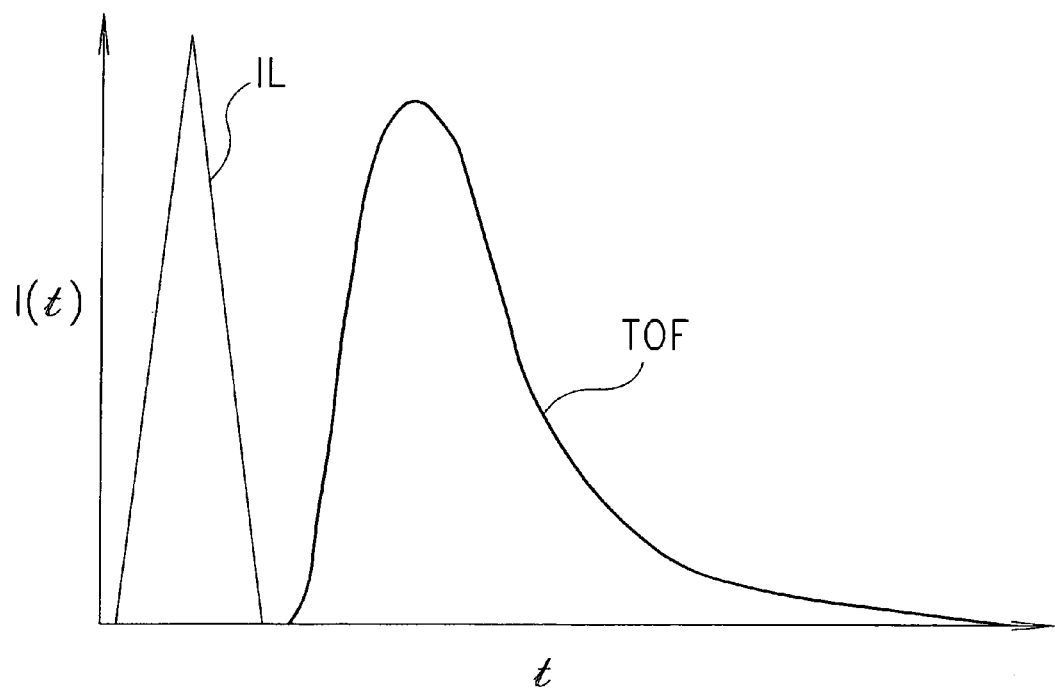
FIG. 2a is a graph illustrating a time domain measurement of a photon time-of-flight distribution resulting from an incident light pulse in a scattering media.

Referring back to FIG. 1, it should be appreciated that the length of scattering path SP is longer than the straight, direct pathway from fiber 30 to fiber 36. This pathlength increase due to the scattering media also results in a comparatively longer propagation time or "time of flight." Because photons typically travel along many different paths in a scattering media, the varying times of flight of the photons is usually amenable to description in a time of flight distribution. Thus, in one alternative embodiment, the diffusion equation may be utilized to compare incident light to resulting multiply scattered light in the time domain. For example, FIG. 2a illustrates the relationship between an input light pulse LP of a selected wavelength to a corresponding "time of flight" response, shown as distribution TOF; where the vertical axis represents photon quantity in terms of intensity I(t), and the horizontal axis represents time t. The TOF distribution may be employed to obtain the observed isotropic scattering coefficient by applying the time domain form of the diffusion equation. Typically, time of flight values are in the range of picoseconds to a few nanoseconds.

Figure 2B:
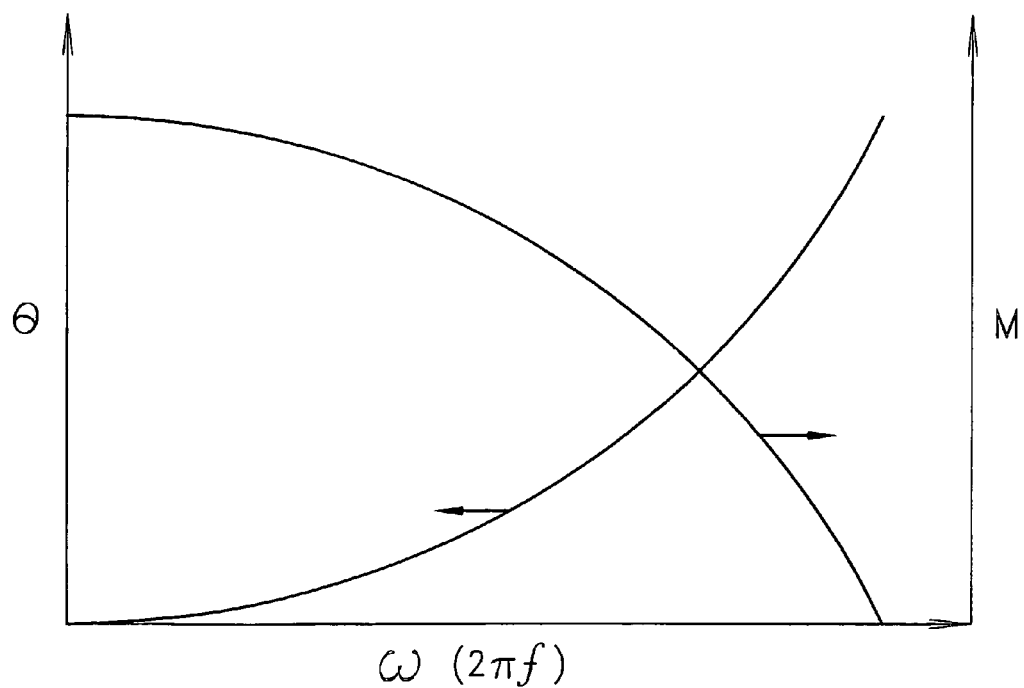
FIG. 2*b* is a graph illustrating the frequency domain measurement of light propagation in a scattering media in terms of phase shift, θ, and amplitude, M.

In comparison, the measurement of intensity modulated light propagation in the frequency domain in accordance with equations (1)–(7) and accompanying text is provided in terms of phase shift $\theta$ and amplitude modulation M in FIG. 2b. Phase shift e is represented by the left vertical axis, amplitude modulation M is represented by the right vertical axis, and frequency is represented by the horizontal axis which increases from left to right. The relationship of frequency to phase shift is characterized by the continuous curve that increases with increasing frequency (as designated by the left-pointing arrow) and the relationship of frequency to amplitude modulation is characterized by the continuous curve which decreases with increasing frequency (as designated by the right-pointing arrow).

It should be appreciated the "time-of-flight" characteristics of a scattering medium alternatively may be described in terms of phase shift and amplitude modulation relative to the modulation frequency. Notably, in both the frequency domain and time domain approaches, an intrinsic optical characteristic or optical property of the particles, such as isotropic scattering and absorption coefficients, may be determined from a time-based propagation measurement of multiply scattered light relative to input light.

In another embodiment, the determination of f(x) and $\phi$ is simplified by assuming an expected form of the PSD Generally, particulate processes can usually be characterized by Gaussian or log-normal distributions, both of which can be represented by proper parametric choices for a Weibull distribution described as follows:

$$f(x) = \frac{c}{b}\left[\frac{x-a}{b}\right]^{c-a} \exp\left[-\left(\frac{x-a}{b}\right)^c\right] \quad (15)$$

where a, b and c describe the peak location, width, and shape, respectively, of the distribution. For this embodiment, d corresponds to $\phi$, and the equation (3) summation approximation becomes:

$$(\mu_s')_j^c = \sum_{i=1}^{s} \frac{3}{2} \frac{Q_{scat}(\lambda_j, n, \chi_i)}{x_i} \quad (16)$$

$$(1 - g(\lambda_j, n, \chi_i))\left\{d\frac{c}{b}\left(\frac{x_i-a}{b}\right)^{(c-a)} \exp\left[-\left(\frac{x_i-a}{b}\right)^c\right]\right\}\Delta_x$$

where the expected range of particle diameter x from $x_{min}$ to $x_{max}$ is determined and incremented into k number of discrete sizes $x_i = x_{min} + (i-1)\Delta x$, $\Delta x = (x_{max} - x_{min})/(z-1)$ for i=1 to z, and the terms $Q_{scat}(\lambda_j, n, x_i)$ and $g(\lambda_j, n, x_i)$ are determined from look-up tables based on $\lambda_j$, n, $x_i$.

Using Newton's method, the updates based estimation of the a, b, c, d parameters can be obtained from the resulting system of equations:

$$\mathfrak{J}^T \mathfrak{J} \Delta \zeta = \mathfrak{J}^T[(\mu_s')^o - (\mu_s')^c] \quad (17)$$

where the Jacobian matrix $\mathfrak{J}$ now represents the sensitivity of isotropic scattering coefficients measured at wavelengths j=1,M upon the four parameters (a, b, c and d):

$$\mathfrak{J} = \begin{bmatrix} \frac{\partial(\mu_s')_{\lambda_1}^c}{\partial a} & \frac{\partial(\mu_s')_{\lambda_1}^c}{\partial b} & \frac{\partial(\mu_s')_{\lambda_1}^c}{\partial c} & \frac{\partial(\mu_s')_{\lambda_1}^c}{\partial d} \\ \frac{\partial(\mu_s')_{\lambda_2}^c}{\partial a} & \frac{\partial(\mu_s')_{\lambda_2}^c}{\partial b} & \frac{\partial(\mu_s')_{\lambda_2}^c}{\partial c} & \frac{\partial(\mu_s')_{\lambda_2}^c}{\partial d} \\ M_c & M_c & M_c & M_c \\ \frac{\partial(\mu_s')_{\lambda_M}^c}{\partial a} & \frac{\partial(\mu_s')_{\lambda_M}^c}{\partial b} & \frac{\partial(\mu_s')_{\lambda_M}^c}{\partial c} & \frac{\partial(\mu_s')_{\lambda_M}^c}{\partial d} \end{bmatrix} \quad (18)$$

The elements of the Jacobian are numerically computed using equation (3). The vectors, $(\mu_s')^o$ and $(\mu_s')^c$ contain the observed and computed values of isotropic scattering coefficients at the wavelengths of interest:

$$(\mu_s')^o = ((\mu_s')_{\lambda_1}^o, (\mu_s')_{\lambda_2}^o, \ldots (\mu_s')_{\lambda_M}^o), (\mu_s')^c = ((\mu_s')_{\lambda_1}^c, (\mu_s')_{\lambda_2}^c, \ldots (\mu_s')_{\lambda_M}^c) \quad (19)$$

$\Delta \zeta$ is the vector updating the four parameters, a, b, c and d:

$$\Delta \zeta = (\delta a, \delta b, \delta c, \delta d)^T \quad (20)$$

Thus, the particle sizing task now becomes to recover the four parameters (a, b, c and d) to describe f(x) and $\phi$ using the approach described in connection with loop 540.

In still another embodiment, a low pass filter is employed to smooth the estimate based on the parameters for an expected form of distribution, such as the Weibull distribution. In this embodiment, the size distribution is computed from the parameters and then subjected to a digital low pass filter by averaging over a window of $N^*\Delta x$.

$$f(x_p)^{new} = (1-\xi)f(x_p)^{old} + \frac{\xi}{N^*} \sum_{l=p-\frac{N^*}{2}}^{l=p+\frac{N^*}{2}} f(x_l)^{old} \quad (21)$$

where $\xi$ is a factor between 0 and 1, and the summation is over the N* particle sizes which surround the pth particle size. Current experiments have shown $\xi = 0.35$ to be one preferred condition for the filter. This low pass filter typically enhances the particle size distribution recovery considerably by relaxing the requirement of the selected type of size distribution. It should be appreciated that the wider the distribution, the larger the required filter width for enhanced reconstruction. From the "filtered" f(x), the calculated isotropic scattering coefficient $(\mu_{s'})_j^c$ is computed for updating the Jacobian matrix.

In still a further embodiment, calculation of the inverse solution is improved when the total mass of the particles $M_i$ and the mass density p are known. For this embodiment, the estimation of f(x) and $\phi$ focuses not only on the comparison of observed and calculated isotropic scattering coefficients, but also compares the known total particle mass to the mass obtained as a function of p and the estimates as follows:

$$M_t = \int_0^\infty \rho \frac{1}{12} \pi x^3 [\phi f(x)] dx. \quad (22)$$

For some process configurations "mass balance" may often serve as a process control parameter in addition to PSD and volume fraction. For example, in emulsion polymerization processes, the total mass of monomer dispersed prior to initiation of polymerization is known. Proper reconstruction of the size distribution of the dispersed monomer phase should enable prediction of the total mass of dispersed monomer. Disappearance of the mass of monomer should reappear as mass of polymer. To include this mass balance constraint in the algorithm, we consider it as a constraint in the least squares minimization comparison as follows:

$$\chi^2 = \sum_{j=\lambda_l}^{\lambda_M} [(\mu'_s)_j^o - (\mu'_s)_j^c]^2 + w\left[M_t - \int_0^\infty \rho \frac{1}{12} \pi x^3 \phi f(x) dx\right]^2 \quad (23)$$

where w is a weighting parameter. To efficiently update the estimate and account for the relationship of equation (23), the following Jacobian-based relationship is employed:

$$(\mathfrak{J}^T \mathfrak{J} + \mathfrak{R} + \alpha I)\Delta\varsigma = \mathfrak{J}^T[(\mu_s')^o - (\mu_s')^c] + V \quad (24)$$

where $$\mathfrak{R} = \begin{bmatrix} \frac{\partial V_1}{\partial a} & \frac{\partial V_1}{\partial b} & \frac{\partial V_1}{\partial c} & \frac{\partial V_1}{\partial d} \\ \frac{\partial V_2}{\partial a} & \frac{\partial V_2}{\partial b} & \frac{\partial V_2}{\partial c} & \frac{\partial V_2}{\partial d} \\ \frac{\partial V_3}{\partial a} & \frac{\partial V_3}{\partial b} & \frac{\partial V_3}{\partial c} & \frac{\partial V_3}{\partial d} \\ \frac{\partial V_4}{\partial a} & \frac{\partial V_4}{\partial b} & \frac{\partial V_4}{\partial c} & \frac{\partial V_4}{\partial d} \end{bmatrix} \quad (25)$$

$$V = (V_1, V_2, V_3, V_4)^T \quad (26)$$

$$V_1 = w\left[M_t - \int_0^\infty \rho \frac{1}{12} \pi x^3 \phi f(x) dx\right]\int_0^\infty \rho \frac{1}{12} \pi x^3 \phi \frac{\partial f(x)}{\partial a} dx \quad (27)$$

$$V_2 = w\left[M_t - \int_0^\infty \rho \frac{1}{12} \pi x^3 \phi f(x) dx\right]\int_0^\infty \rho \frac{1}{12} \pi x^3 \phi \frac{\partial f(x)}{\partial b} dx \quad (28)$$

$$V_3 = w\left[M_t - \int_0^\infty \rho \frac{1}{12} \pi x^3 \phi f(x) dx\right]\int_0^\infty \rho \frac{1}{12} \pi x^3 \phi \frac{\partial f(x)}{\partial c} dx \quad (29)$$

$$V_4 = w\left[M_t - \int_0^\infty \rho \frac{1}{12} \pi x^3 \phi f(x) dx\right]\int_0^\infty \rho \frac{1}{12} \pi x^3 \phi \frac{\partial f(x)}{\partial d} dx \quad (30)$$

This mass balance constraint serves as an additional regularization scheme and typically provides further stabilization.

Figure 3:
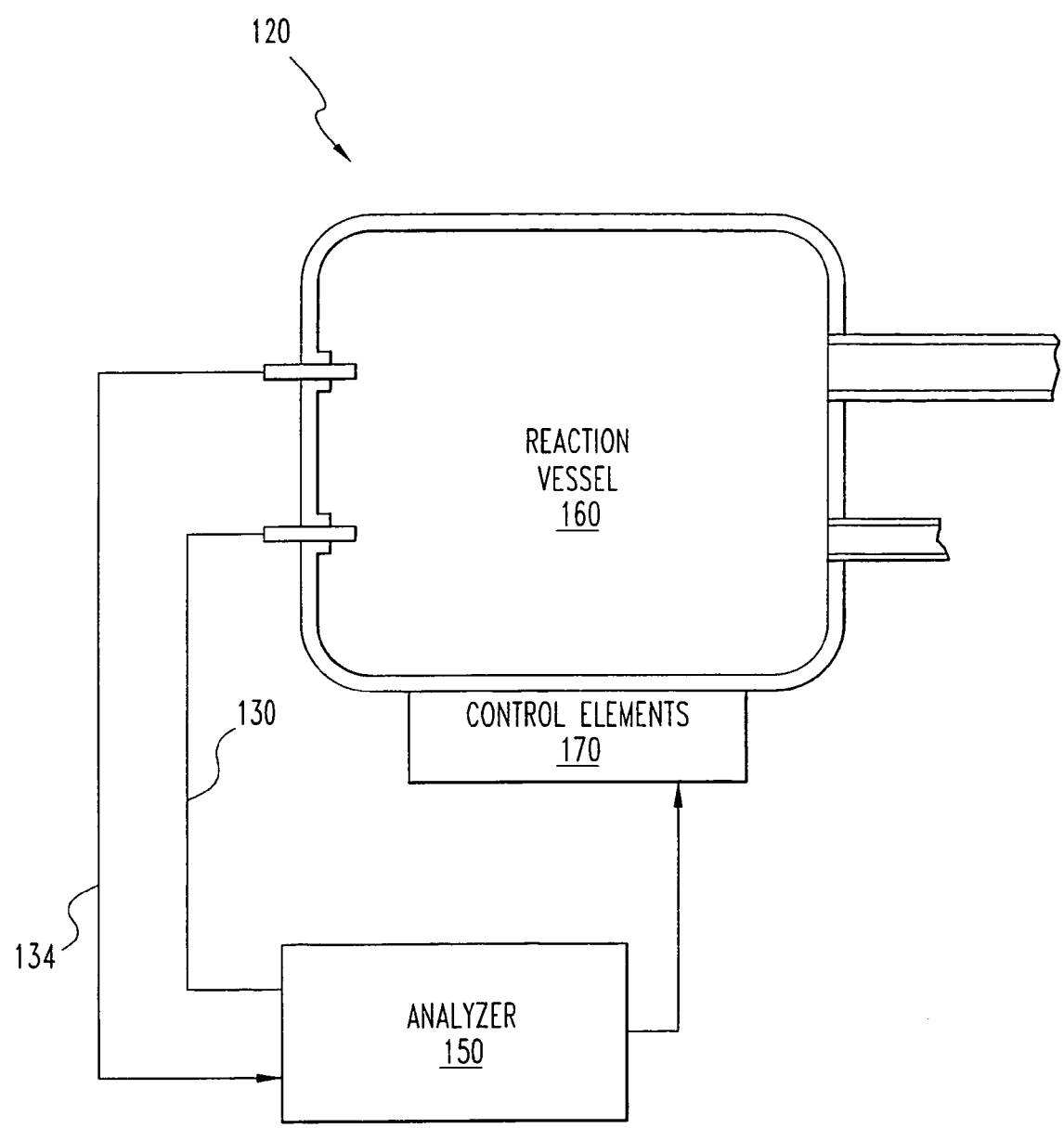
FIG. 3 is a schematic view of a chemical process control system of another embodiment of the present invention.

FIG. 3 depicts system 120 of an alternative embodiment of the present invention is depicted. System 120 includes analyzer 150 coupled to reaction vessel 160 by fibers 130 and 134. Analyzer 150 is configured to determine PSD and volume fraction for particles dispersed in a fluid medium in vessel 160 in accordance with the present invention. Generally, the optimum number and size of the wavelengths selected for interrogation depends on the nature of the particles, medium, and process involved. Furthermore, it has been discovered that typically fewer wavelengths may be required to determine volume fraction as compared to PSD for a given arrangement.

Analyzer 150 includes a light source configured to deliver light to vessel 160 via fiber 130. This light source may resemble source 21 of system 20, but preferably is a lamp-based or laser diode array system configured to provide light of a desired time-varying intensity at selected wavelengths. In one embodiment, system 120 includes an array of laser diodes which each correspond to a desired wavelength suitable for the particular process and material being interrogated in vessel 160. For this embodiment, the diodes are configured to provide incident (output) light with a sinusoidally modulated intensity. In other embodiments of the present invention, the light source arrangement is configured to provide wavelengths and time-varying intensity suitable for interrogation of the particular process being monitored using techniques known to those skilled in the art.

Analyzer 150 also includes optical fiber 134 to detect re-emitted light from the particles in vessel 160 after multiple scattering. It is preferred that analyzer 150 be of rugged design suitable for industrial applications. Analyzer 150 includes a processor configured to execute software to determine values representative of PSD or volume fraction in accordance with the present invention. Furthermore, analyzer 150 is also operatively coupled to control elements 170 which are used to regulate processing in vessel 160. By way of non-limiting example, elements 170 may include valves, heaters, or agitation devices electronically regulated by analyzer 150. Analyzer 150 is further configured with appropriate programming and interfaces to provide one or more output signals to control elements 170 as a function of PSD or volume fraction. Thus, system 120 provides a closed loop feedback control system capability for regulating chemical processes from on-line measurement of PSD and/or volume fraction.

Systems 20 and 120 of FIGS. 1 and 3, respectively, are described with corresponding light source fibers 30, 130 and detecting fibers 36, 136 geometrically arranged to approximate infinite boundary conditions—such that light travelling from fibers 30, 130 to fibers 36, 136 does not encounter a substantial boundary. Equations (6) or (7) are applied to determine the isotropic scattering coefficient $\mu_s'$ and the absorption $\mu_a$ under such infinite boundary conditions. In other embodiments, the present invention may be readily adapted to different boundary conditions. For example, in one alternative embodiment, a processing chamber or passageway containing the scattering media may be interrogated by detecting multiply scattered light that is reflected or backscattered by the media through a "viewing window" arrangement instead of directly immersing fibers in the media. This arrangement results in a reflectance boundary condition. The present invention may be adapted using techniques known to those skilled in the art to accommodate this reflectance geometry or such other boundary conditions as may arise from a particular probe arrangement.

When the concentration of particles suspended in a medium is low (e.g. <2%), the particles act independently with regard to light scattering; however, as the concentration increases, interactions between suspended particles become more significant. These particle-to-particle interactions may impact accuracy of the f(x) and φ determination in accordance with the present invention. Thus, a particle interaction parameter which accounts for concentration-dependent particle interactions that influence light scattering properties is desirable. Preferably, the determination of this particle interaction parameter may be incorporated into techniques of the present invention for determining f(x) and φ.

For one preferred embodiment, a structure factor S(q) for the particles has been found to be suitable as the particle interaction parameter. In this embodiment, the structure factor S(q) is introduced by modifying the isotropic scattering coefficient ($\mu_s'$) determination of equation (3) as follows:

$$\mu_s' = \int_0^\infty \frac{3}{2x} \left[ \int_0^\infty 2\pi q_{scat}(n, \lambda, r, \theta) \pi r^2 (1 - g(n, \lambda, r)) S(q) \phi (1 - g(n, \lambda, x)) \sin(\theta) \, d\theta \right] \phi f(x) dx \quad (31)$$

where: q=equals $[(4\pi n/\lambda_j)\sin(\theta/2)]$ and $q_{scat}$ is the angular scattering efficiency. The structure factor S(q) accounts for nonrandom particle structure within the fluid that typically varies with concentration of the particles in the medium. For example, the electrostatic charge on suspended particles generally influences spacing and organization of substantially concentrated particles in a fluid, which in turn influences light scattering. For low concentrations, these forces are usually negligible, so the particles may be treated as random scatterers with S(q)=1. For a structure factor of unity (S(q)=1), the calculation of isotropic scattering coefficients $\mu_s'$ at each wavelength of interest is the same in equations (3) and (31). For higher concentrations, S(q) typically varies with the structure imparted by the particle interactions.

Figure 14:
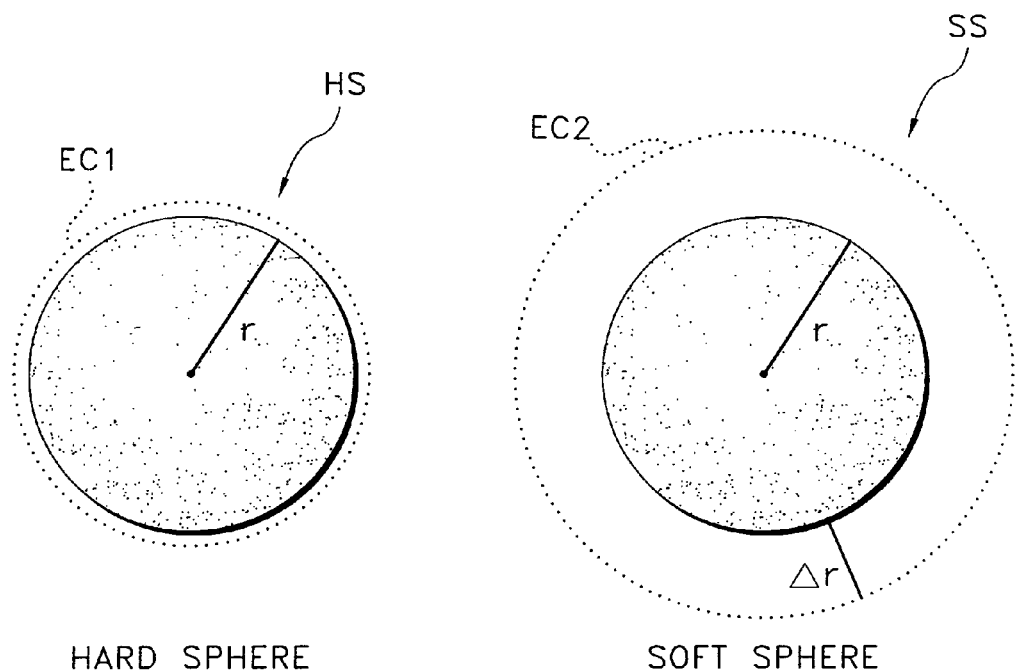
FIG. 14 is a comparative schematic illustration of selected aspects of particle-to-particle interaction structure factor models of the present invention.

One approach to ascertaining an appropriate S(q) is to treat particles as hard spheres of radius r as represented in FIG. 14 by particle hard sphere HS. For a hard sphere, the electrostatic charge resides on the surface, as represented in FIG. 14 by broken line EC1. For this approximation, the Percus-Yevick (P-Y) hard sphere model may be employed to predict S(q) as follows:

$$\frac{1}{S(q)} = \quad (32)$$

$$1 + \frac{24\varphi}{x^3} \left\{ \begin{array}{l} A(\sin x - x\cos x) + B\left[\left(\frac{2}{x} - 1\right)x\cos x + 2\sin x - \frac{2}{x}\right] \\ + \frac{\varphi A}{2}\left[\frac{24}{x^3} + 4\left(1 - \frac{6}{x^2}\right)\sin x - \left(1 - \frac{12}{x^2} + \frac{24}{x^4}\right)x\cos x\right] \end{array} \right\};$$

where: σ is the diameter of the particle determined from f(x); x=qσ; φ=(πNDσ³/6); ND=number density of particles determined from σ and φ; A=$[(1+2\phi)^2/(1-\phi)^4]$; and B=$[-3\phi(\phi+2)^2/2(1-\phi)^4]$. It should be noted that S(q) is a function of f(x) and φ.

Figure 13:
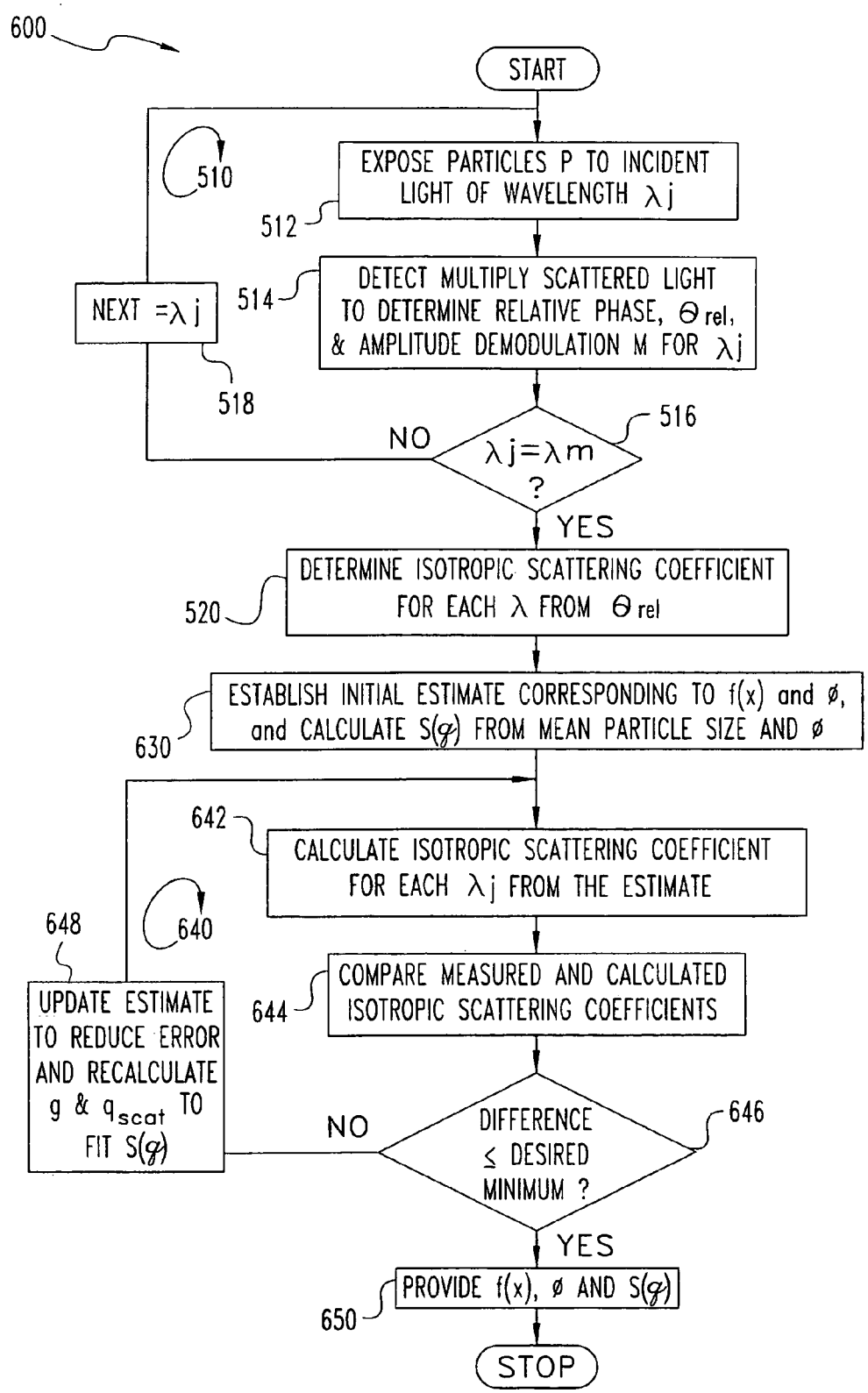
FIG. 13 is a flow chart illustrating another process of the present invention capable of performance, for example, by the systems of FIGS. 1 and 3.

FIG. 13 is a flow chart of process 600 which may be used to determine f(x), φ, and S(q). Process 600 may be performed using system 20, system 120, or such other system as would occur to one skilled in the art. Stages 510–520 of process 600 are the same as the like numbered stages of process 500 described in connection with FIG. 2. After stage 520, stage 630 of process 600 is encountered. In stage 630, f(x) and φ are estimated and S(q) is calculated. Notably, the determination of S(q) is dependent on f(x) and φ estimates for this embodiment. The S(q) calculation utilizes the mean particle diameter for σ as determined from the f(x) estimate, and the number density ND as determined from the f(x) and volume fraction φ estimates. Also, g and $q_{scat}$ are initially determined to fit the calculated S(q) to the measured isotropic coefficient $\mu_s'$ and absorption coefficient $\mu_a$ in accordance with a summation approximation of equation (31) for each wavelength $\lambda_j$.

Next, loop 640 is entered. In loop 640, stage 642 is encountered in which isotropic scattering coefficients for each wavelength $(\mu_s')_j^c$ are calculated through the summation approximation of equation (31) for all wavelengths using the estimates of f(x) and φ, and the corresponding calculated values of S(q), g, and $q_{scat}$. After stage 642, control flows to stage 644 to determine $\chi^2$ as described in connection with stage 544 of process 500. The $\chi^2$ of observed and calculated coefficients is then compared to an error threshold in conditional 646 to determine if the current estimates of f(x) and φ are suitable for output. If conditional 646 is satisfied, control flows to stage 650 to output f(x), φ, and S(q). If conditional 646 is not satisfied, control flows to stage 648.

In stage 648, the estimation of f(x) and φ is updated. This update also includes recalculation of g and $q_{scat}$ based on the current S(q) value. Once updates are performed in 648, loop 640 closes back on stage 642 to provide updated calculations of the corresponding isotropic scattering coefficients. Loop 640 is iteratively executed until the $\chi^2$ difference is minimized to an acceptable level. The particle size distribution f(x), the volume fraction φ, and structure factor S(q) may be output in stage 650. Aside from the improved accuracy of size distribution estimation and volume fraction at high particle concentrations, the structure factor S(q) is useful in ascertaining information about the behavior of colloidal suspensions and emulsions. For example, the structure factor alone is useful in monitoring colloidal suspensions and predicting shelf-life of emulsions with respect to phase separation. In other embodiments, different particle structure factor models may be employed other than the P-Y hard sphere model as would occur to those skilled in the art.

Figure 15:
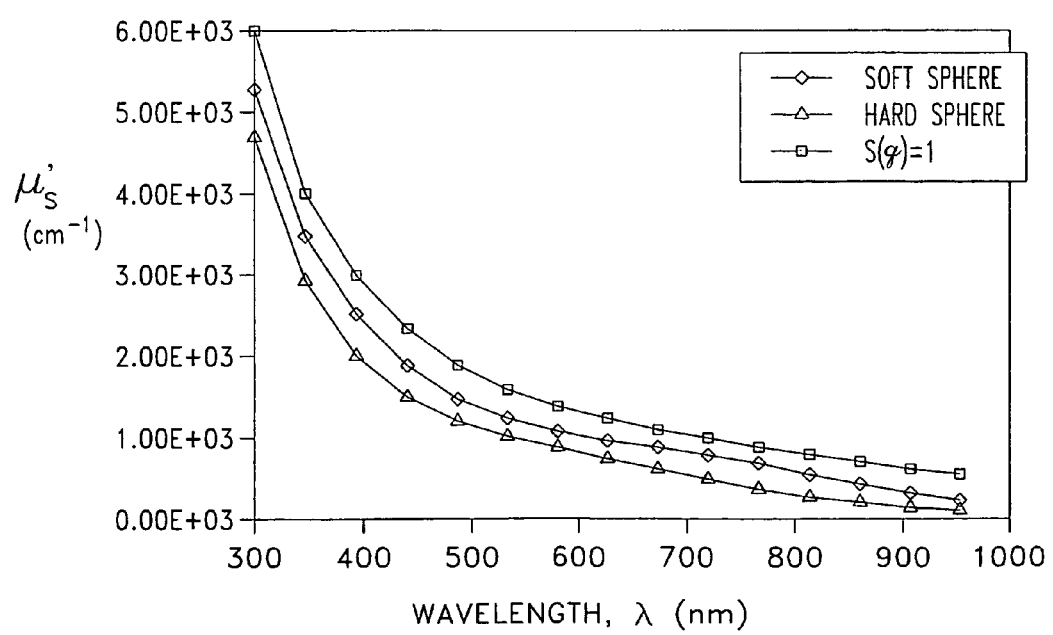
FIG. 15 is a graph comparing selected structure factor models in terms of isotropic scattering coefficient and light wavelength.

In one such alternative structure factor model, the hard sphere model is modified to account for electronic affects beyond the particle surface. This phenomenon is particularly substantial for lower concentrations of electrolytes, where particle interactions are still significant. FIG. 14 comparatively represents this modification as a soft sphere SS next to hard sphere HS. Soft sphere SS has a "soft" outer shell region corresponding to the interactive reach of the particle beyond its surface. This "soft" region is designated by the radial extension increment Δr and accounts for the electronic forces extending beyond the surface of the particles. The effective electrostatic charge EC2 is shown as a broken line at r+Δr. The sum r+Δr is treated as the "equivalent" hard sphere radius for the P-Y model which is otherwise applied in the same way as described above. FIG. 15 depicts the relationship of the isotropic scattering coefficient to light wavelength for the soft sphere model (diamond-shaped data points), the hard sphere model (triangular-shaped data points), and the unity structure factor, S(q)=1 (square-shaped data points).

Regardless of the structure factor model selected, any of the embodiments previously described and any such variations as would occur to those skilled in the art may be adapted to incorporate the structure factor technique. By way of nonlimiting example, the mass balance constraint described in connection with equations (22)–(30) or the Weibull distribution simplification described in connection with equations (15)–(20) may be included in a process to determine a structure factor or effective hard sphere radius that accounts for the degree of particle interactions. Moreover, besides structure factor, other particle interaction parameters may be selected and applied in accordance with the present invention to account for variation in light scattering properties with particle concentration due to particle-to-particle interactions. Such particle interaction parameters generally characterize nonlinearity between a scattering property of the particles, such as the isotropic scattering coefficient, and the particle concentration level.

EXPERIMENTAL SECTION

The present invention will be further described with reference to the following specific examples. It will be understood that these examples are illustrative and not restrictive in nature.

Experimental measurements to determine PSD and volume fraction where conducted with a instrumentation configuration substantially similar to system 20. This instrumentation included a 10W argon ion laser (Beam-Lok 2060, Spectra Physics, CA) which pumped a picosecond pulsed Titanium:Sapphire laser (model 3950B Tsunami, Spectra Physics, Mountain View, Calif.). The Ti:Sapphire laser produced an optical pulse train of equally spaced light pulses of 2 psec FWHM at a repetition rate of 80 MHz. The output beam was sent to a pulse picker (model 3980, Spectra Physics) having an AOM crystal to produce a pulse repetition rate of 4 MHz at 2 ps FWHM and a SHG crystal to provide for light wave frequency doubling (wavelength halving). As a result, wavelengths from 720 to 900 nm, and from 360 to 450 nm were available for selection. The average power exiting the AOM crystal and the frequency-doubler (SHG crystal) was 50 mW and 10 mW, respectively. Depending upon the wavelength desired, the pulsed laser beam from the AOM or frequency doubler was sent to a glass slide beam splitter 28 that directed approximately 20% of the light to a reference sensor, photomultiplier tube (PMT) (Hamamatsu R928, Hamamatsu, Japan), via a 1000 μm optical fiber (HCP-M1000T-08, Spectran, Avon, Conn.). The remaining light was directed to the scattering sample by another optical fiber which was held stationary and vertical in a clear acrylic cylindrical tank having a 9 inch outer diameter and 8 inch height. The tank was filled with a sample having particles suspended in a fluid medium.

The light which propagated from the source fiber within the multiple scattering medium was collected by another fiber held vertically in place in the tank. The detected light was then delivered to a sample sensor, also a PMT, via an optic fiber. Fourier analysis of the 4 MHz pulse train delivered to the sample and reference PMT's yielded a series of harmonic intensity-modulation frequencies at multiples of 4 MHz, which upon application of heterodyne detection techniques permitted isolation of the individual intensity-modulated frequencies. Heterodyning was performed by gain modulating the reference and sample PMTs at a harmonic of the laser repetition rate plus an offset cross-correlation frequency of 100 Hz. Gain modulation was accomplished using a commercial electronics package (ISS, Champaign, Ill.) and a −3 dBm RF signal from a frequency synthesizer (Marconi Instruments Signal Generator 2022A) amplified by a power amp (model 1403LA, ENI, Rochester, N.Y.). The resulting 100 Hz electronic signal from the heterodyned PMTs provided the frequency domain phase-shift and amplitude modulation information. A conventional data acquisition module (ISS, Champaign, Ill.) was employed in a 486 IBM compatible personal computer to collect the measurement data.

By sweeping the RF signals at varying harmonics of the laser repetition rates, measurements of phase-shift $\theta(\omega)$ and amplitude demodulation $M(\omega)$ of a multiply scattered photon density wave propagating at varying modulation frequencies were detected with the sample PMT relative to the incident light detected with the reference PMT. In order to obtain values of relative phase-shift, 0 rel, measurements were conducted as the detecting fiber optic was moved with micrometer precision to distances of 1.0, 1.5, and 2.0 cm away from the source fiber optic. At each source-detector separation, measurements were conducted at 10 modulation frequencies ranging from 24 to 240 MHz. Relative phase-shift between any two source-detector separations was determined by subtracting the phase-shift measured at the farthest separation from that measured as a closer separation. By fitting experimentally measured relative phase-shift at varying modulation frequencies to equation (7) using Levenberg-Maraquardt non-linear least square regression, parameter estimates of $\mu_a$ and $\mu_s'$ were obtained.

Three polydisperse samples of polystyrene microsphere suspensions were characterized using frequency domain measurements of multiply scattered light with this instrumentation. The three polystyrene samples were obtained from DOW Chemical Company of Midland, Mich. and designated PP722, PP755, and PP788 with mean particle diameters of 0.5763, 0.2954, and 0.1685 microns, respectively, as determined by independent DLS measurements (Microtrac Ultrafine Particle Analyzer, Honeywell, Leeds and Northrup, St. Petersburg, Fla.). The concentration of solids for PP722, PP755, and PP788 were 47.95%, 52.74%, and 46.03% solids by volume respectively as determined through evaporation measurements. The samples were diluted about 50 times with deionized ultrafiltered water to obtain samples of approximately 1% solids by volume. This concentration results in an opaque solution suitable to multiply scatter light.

Figure 4:
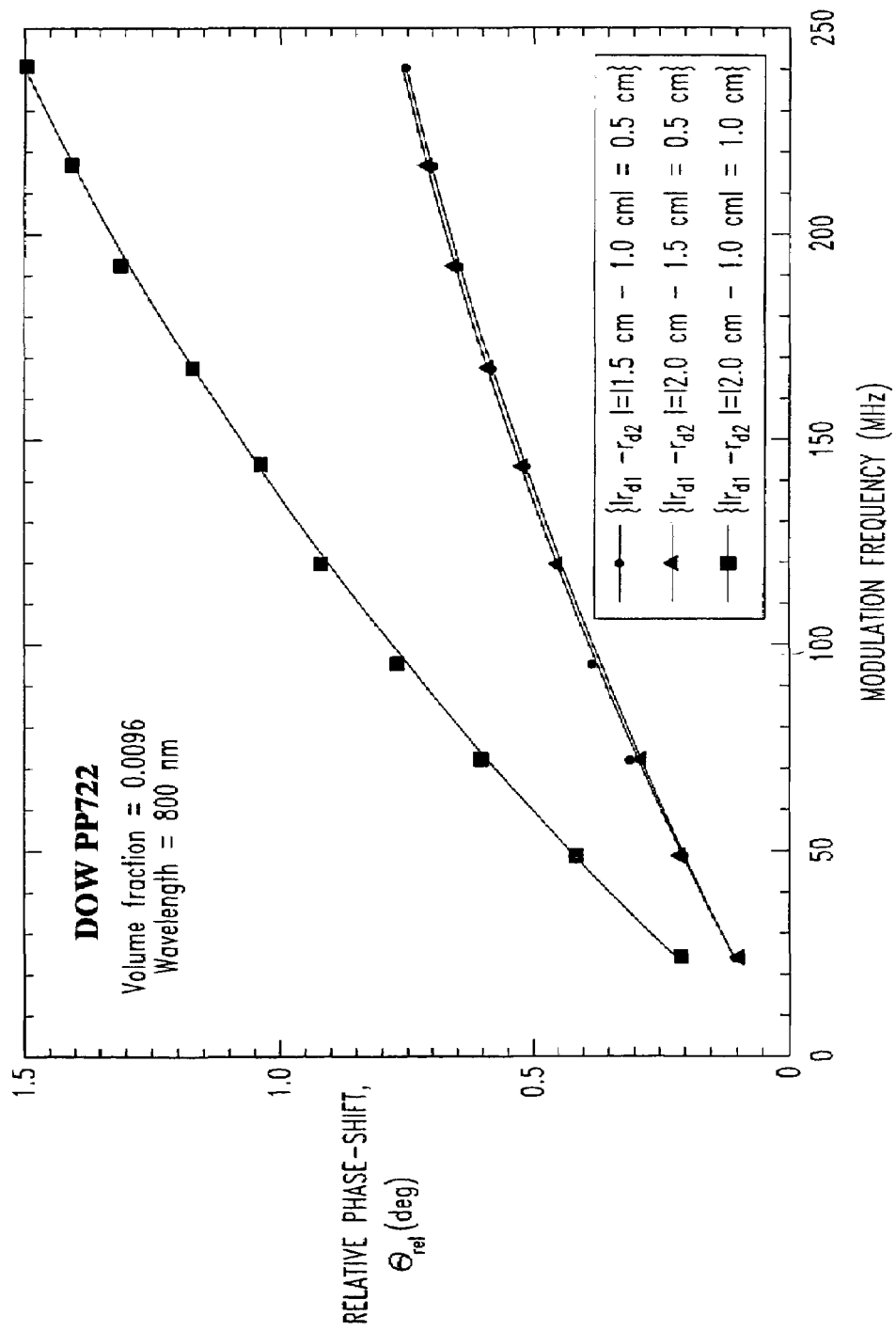
FIG. 4 is a graph depicting the relationship between phase shift and modulation frequency for a dispersion of DOW PP722 particles.

FIG. 4 illustrates the typical measurements of relative phase-shift, $\theta_{rel}$ on 0.96% by volume PP722 sample as a function of modulation frequency at a wavelength of 800 nm. Measurements were conducted with source-detector separations $|r_s-r_d|$ of 2.0, 1.5, and 1.0 cm. Consequently, relative phase-shift was reported at relative detector—detector separations $|r_{d1}-r_{d2}|$ of 1.0 and 0.5 cm. It is noteworthy that the two sets of phase-shift data recorded for each of the 0.5 cm separations were approximately the same, and the relative phase-shift for the 1.0 cm separation was about twice as large as the relative phase shift corresponding to the 0.5 cm separations. This dependence of phase shift on the relative separation of the source and detection sites is consistent with presence of the $|r_{d1}-r_{d2}|$ term in equation (7).

Figure 5:
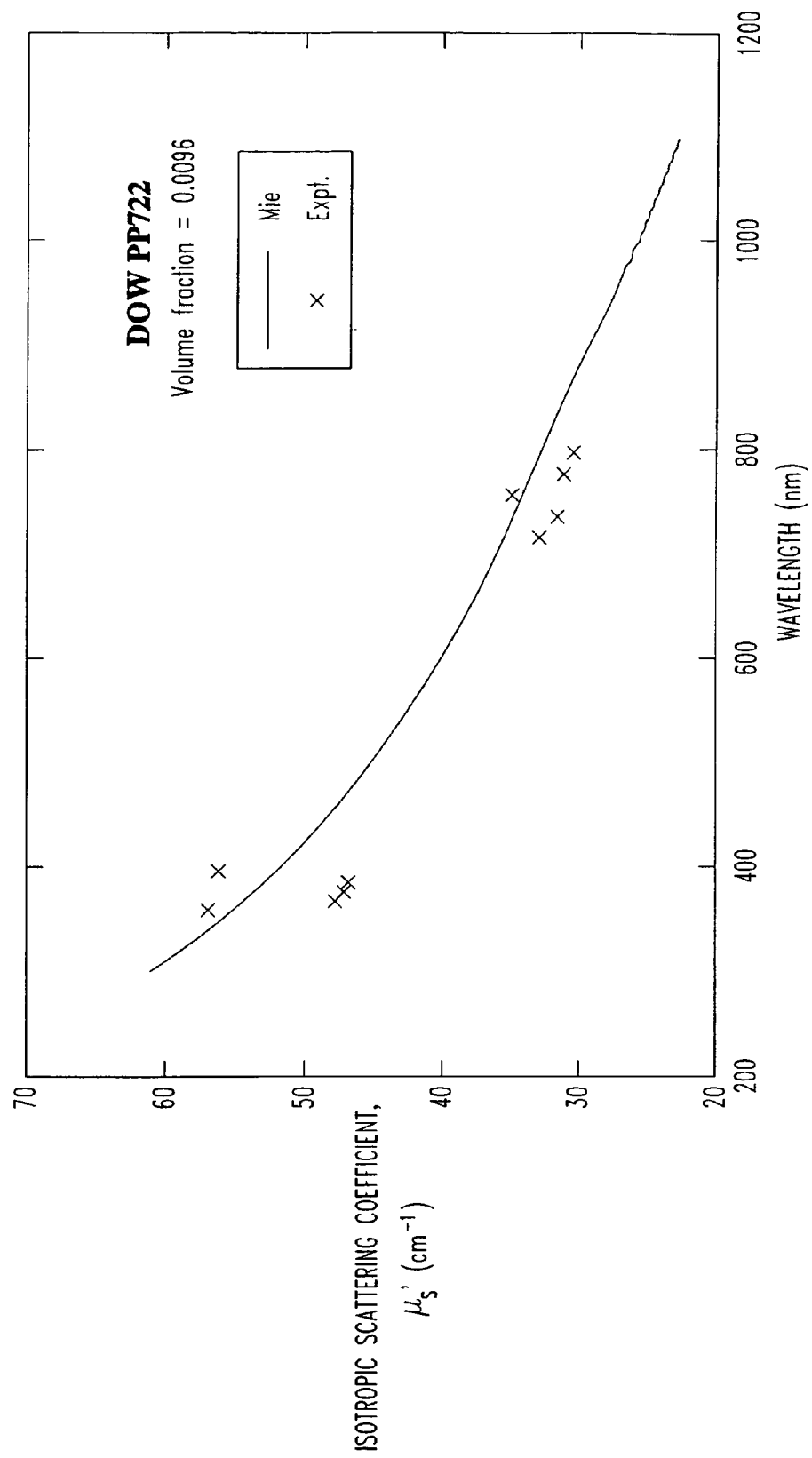
FIG. 5 is a graph depicting the isotropic scattering coefficient for a dispersion of DOW PP722 particles as a function of wavelength.

FIG. 5 graphically depicts experimental values (x symbols) for isotropic scattering coefficients obtained for the PP722 sample from measurements of multiply scattered light at 10 wavelengths between 360 and 800 nm. Expected values (solid line) predicted by Mie theory were calculated with equation (3) from experimental volume fraction and PSD. These measurements were conducted without the use of any external reflectance or calibration standard.

The f(x) and φ for each of the three polydisperse suspensions were determined assuming a Weibull distribution both with and without the mass conservation constraint. The initial estimates of the reconstruction parameters a,b,c,d were up to 100% greater than the output parameters. The particle size distributions, f(x), and volume fraction, φ, required 5 iterations until the function $\chi^2$ reached a desired minimum value. Computational time for each inverse solution required a few seconds on a SunSparc 10 Workstation using the data gathered by the IBM compatible system. The 486 based IBM compatible computer and SunSparc 10

Workstation collectively provide one example a processor suitable for use with the present invention; however, in other embodiments, a single piece of dedicated equipment, or other arrangement is envisioned as would occur to one skilled in the art.

Figure 6:
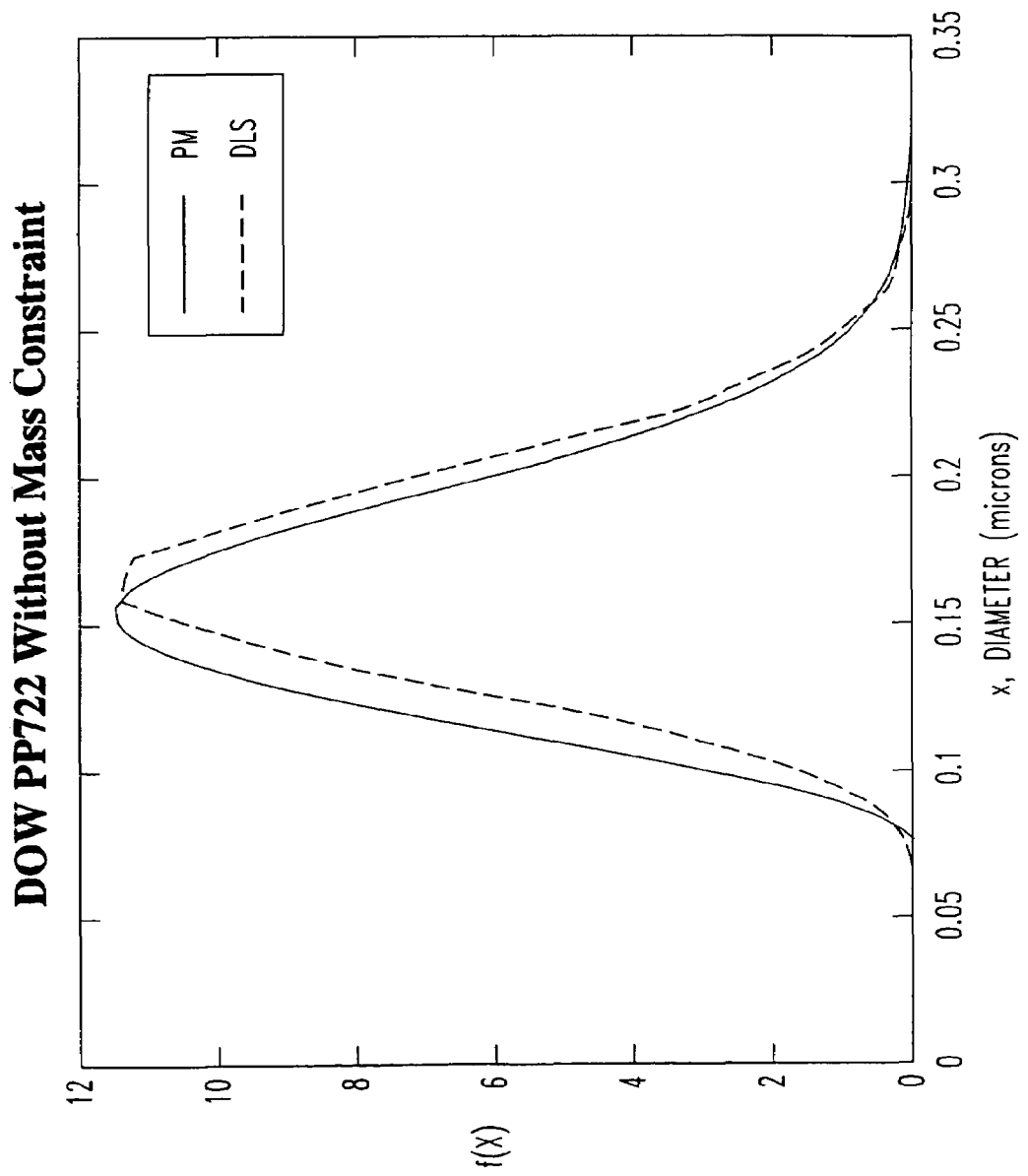
FIGS. 6–8 are graphs depicting size distribution for DOW PP722, PP755, and PP788 particle dispersions without a mass balance constraint, respectively.
Figure 7:
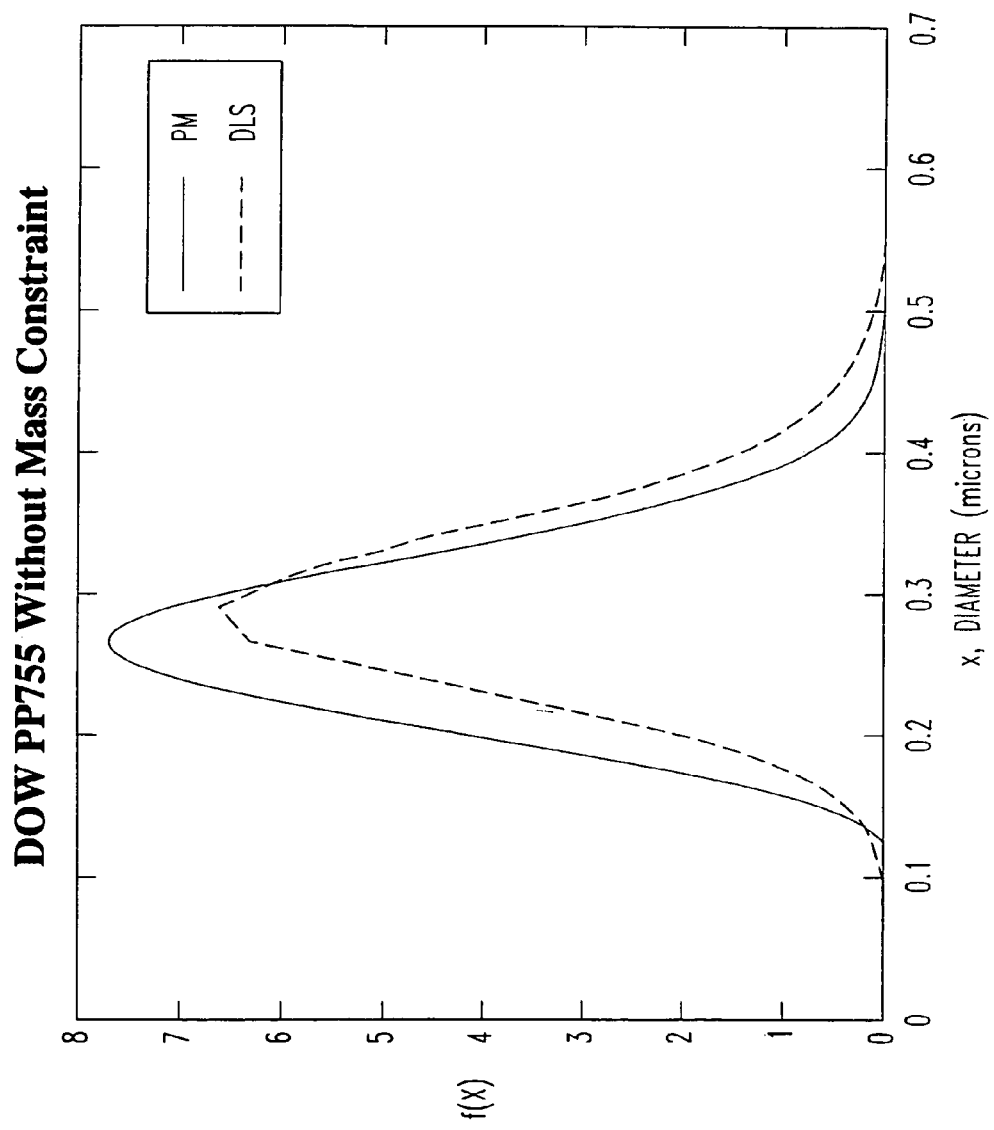
Figure 8:
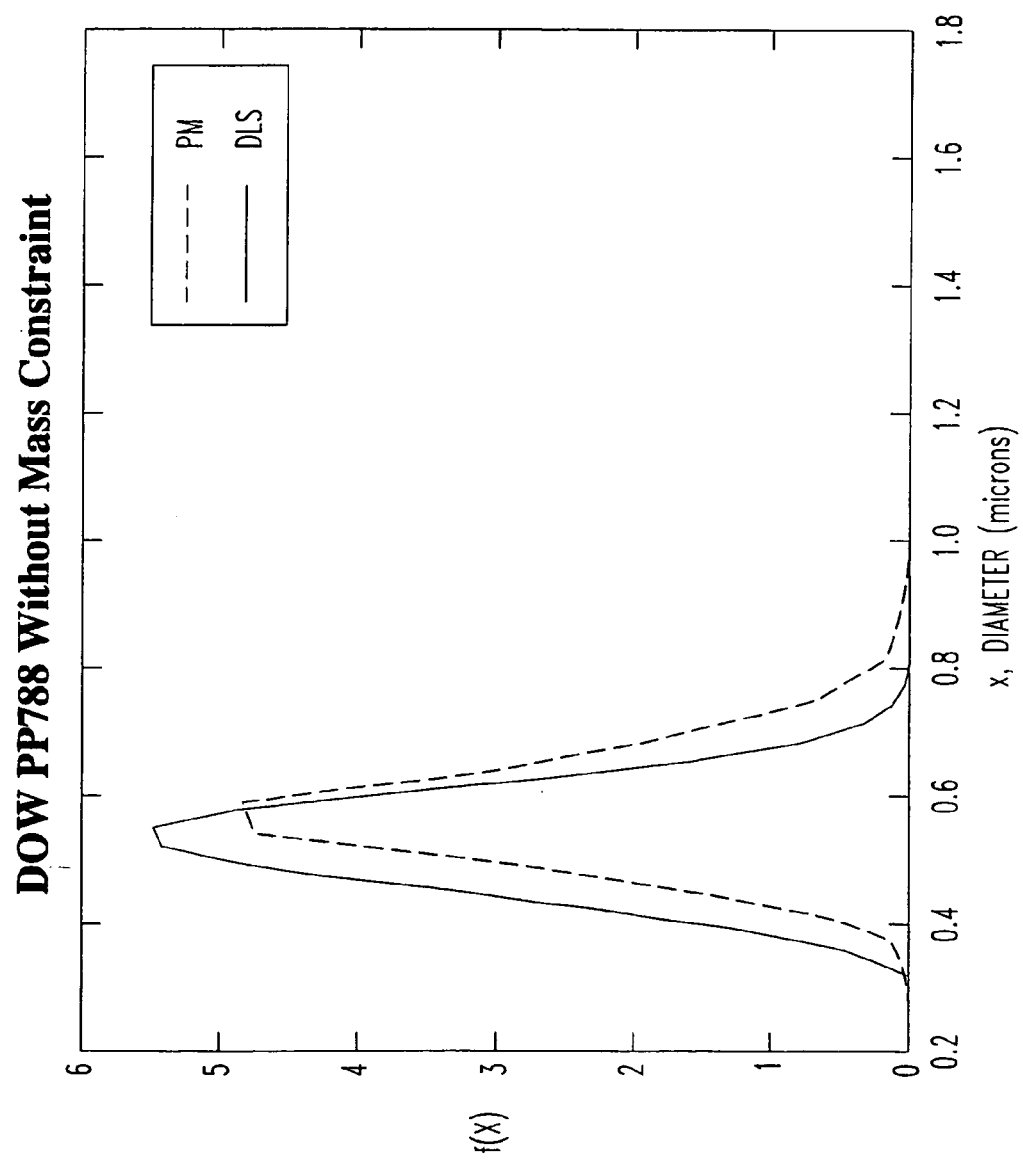

FIGS. 6 through 8 show reconstructed particle size distributions from experimental measurements for the three different suspensions without the mass balance constraint. The solid lines (PM) denote the reconstructed values from the photon migration measurements of multiply scattered light while the dashed lines represent the size distribution obtained from DLS for comparison. Table 2 presents the volume fraction determination for the three different suspensions, as follows:

TABLE 2

Solids volume fractions for suspensions PP722, PP755 and PP788 obtained without mass balance constraint.

| | Values of $\phi$ from Photon Migration (%) | Values of $\phi$ from DLS (%) |
|---|---|---|
| PP722 | 1.16 | 0.95 |
| PP755 | 1.82 | 1.53 |
| PP788 | 0.75 | 0.63 |

Figure 9:
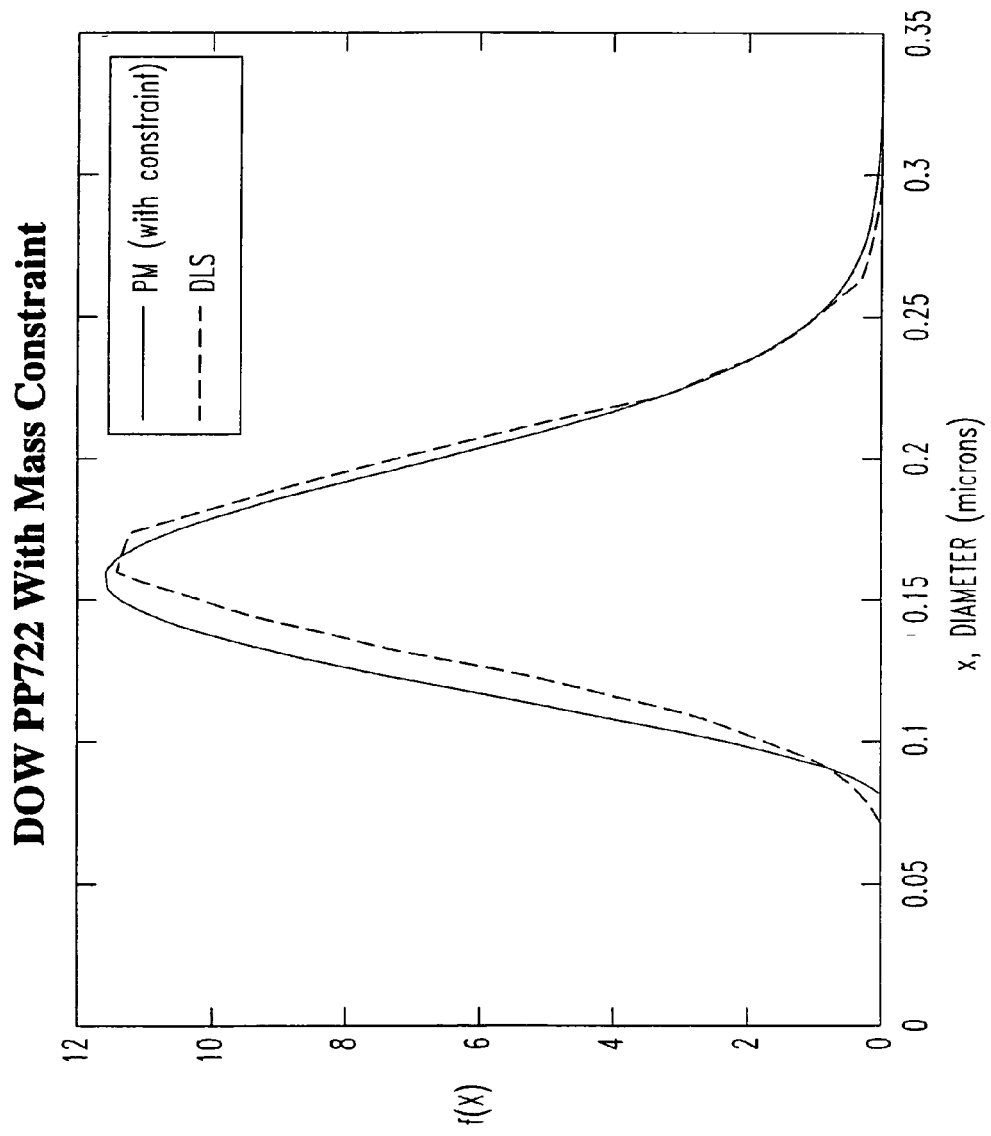
FIGS. 9–11 are graphs depicting size distribution for DOW PP722, PP755, and PP788 particle dispersions with a mass balance constraint, respectively.
Figure 10:
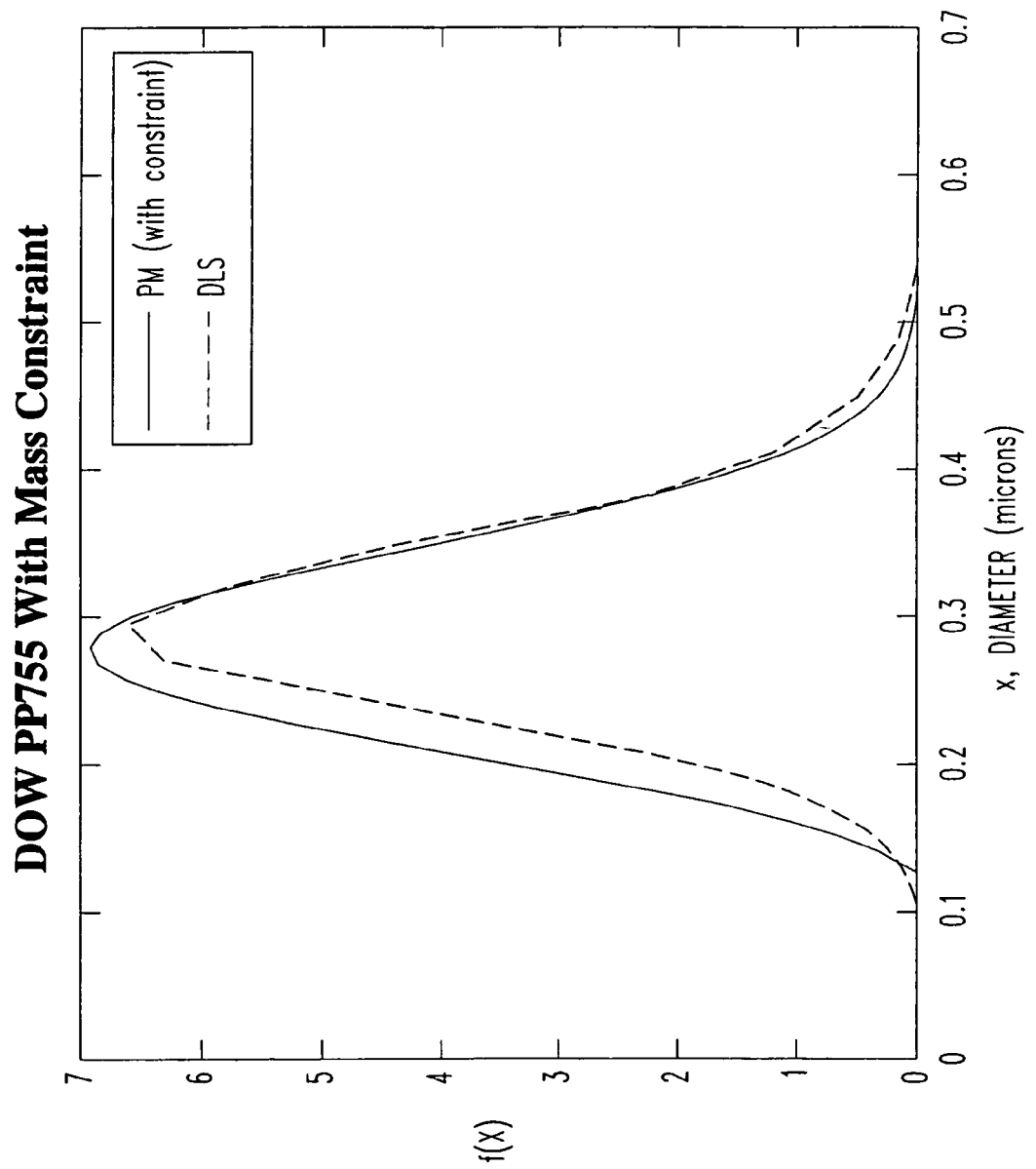
Figure 11:
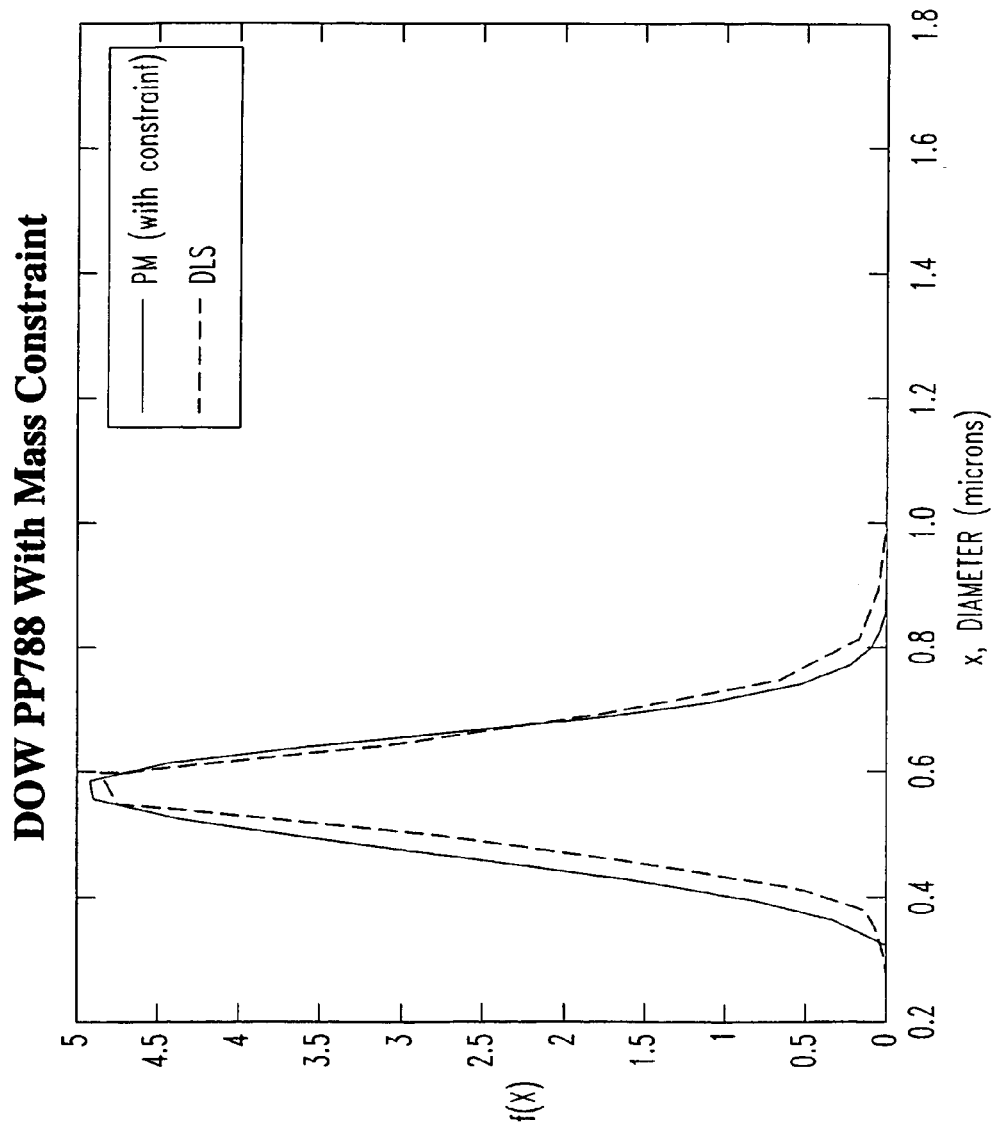

FIGS. 9 through 11 display the reconstructed particle size distributions from experimental measurements for three different suspensions with the additional constraint of mass balance. The weighting parameter used for obtaining these results was a constant of 0.1. It has been discovered that a weighting parameter in the range between 0.01 and 0.2 works well for these samples. Table 3 presents the results from the volume fraction calculations for the three different suspensions as follows:

TABLE 3

Solids volume fractions for suspensions PP722, PP755 and PP788 obtained with mass balance constraint.

| | Values of $\phi$ from Photon Migration (%) | Values of $\phi$ from DLS (%) |
|---|---|---|
| PP722 | 0.98 | 0.95 |
| PP755 | 1.61 | 1.53 |
| PP788 | 0.67 | 0.63 |

Figure 12:
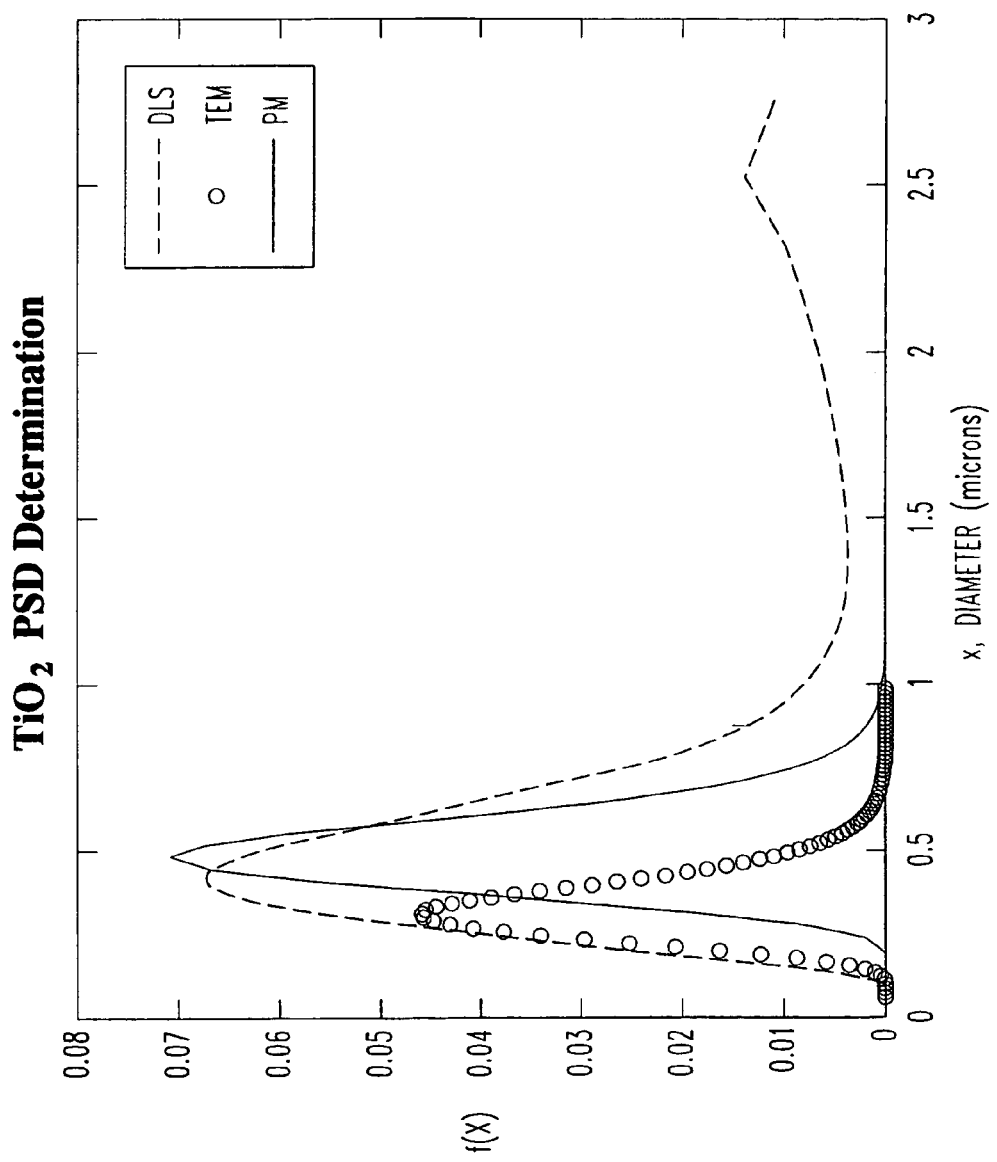
FIG. 12 is a graph depicting size distribution for an aqueous dispersion of $TiO_2$ particles.

FIG. 12 illustrates a Photon Migration (PM) measurement of multiply scattered light to experimentally determine PSD (solid line) for an aqueous $TiO_2$ suspension following a procedure similar to the polystyrene suspensions described above. For comparison, size distributions obtained from Dynamic Light Scattering (DLS) (dashed line) and determined from Transmission Electron Microscopy (TEM) (circle symbols) are shown. It should be noted that the size distributions obtained from photon migration measurements straddled those obtained from DLS and TEM. The nonspherical nature of $TiO_2$ particles does not appear to appreciably detract from the relative accuracy of the PSD determination.

Figure 12B:
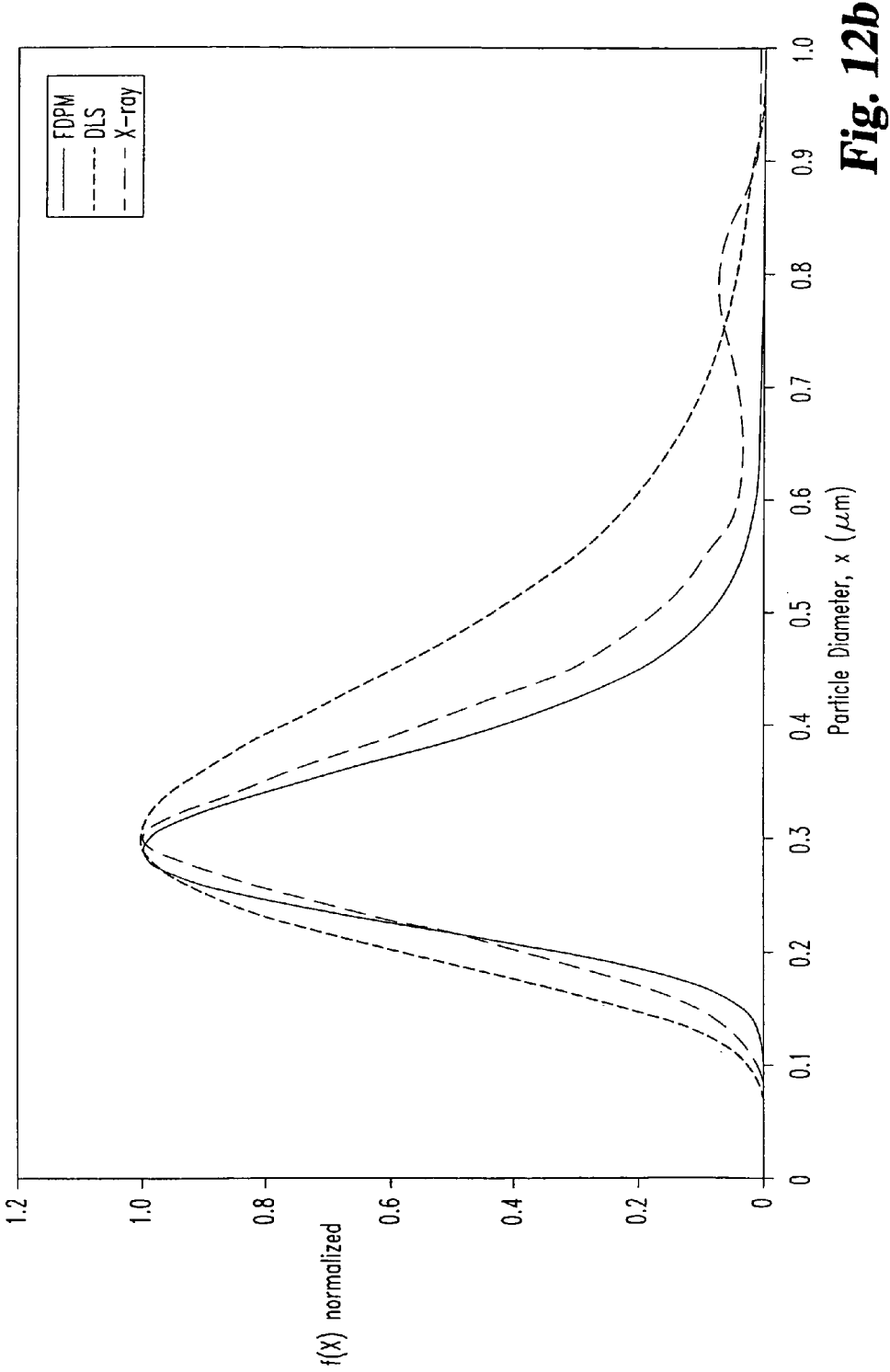

FIGS. 12a–12b comparatively illustrate size distribution determinations using Frequency Domain Photon Migration (FDPM) analysis (solid line) of the present invention, Dynamic Light Scattering (DLS) (short dashed line), and X-ray scattering (long dashed line) for each of two samples of titanium dioxide suspensions, designated S1 and S2, respectively. For the purpose of FDPM measurements, 1000 milliliters (ml) of each sample was placed in a 14.6 centimeter (cm) cylinder glass vessel with an inside diameter of 11.1 cm. Sinusoidally modulated light was deliver to, and collected from each sample via optical fibers of 1000 micrometers in diameter. Both the source and the detector optical fibers were placed parallel to the axis of the cylinder with their tips close to the center of the vessel. Phase shift and amplitude modulation was measured over a modulation frequency range of about 16 megahertz (MHz) to 240 MHz. Relative phase shifts were calculated corresponding to relative source-detector separations ranging form 0.1 cm to 0.5 cm. Samples were gently stirred between measurements to prevent any sedimentation. The solution of the diffusion equation (1) for the transport of photons in multiply scattering solution with infinite media boundary condition was applied to the data of relative phase shifts at different modulation frequencies. Upon applying Marquardt-Levenberg nonlinear regression analysis to this data, isotropic scattering coefficients ($\mu_s'$) were obtained at seventeen different wavelengths ranging from 400 nanometers (nm) to 900 nm. Particle size distribution, f(x), and volume fraction, $\phi$, were determined from these values in accordance with the present invention for samples S1 and S2 corresponding to FIGS. 12a and 12b, respectively. A log-normal Gaussian distribution was assumed for f(x) in both cases. The mean size and standard deviation for samples S1 and S2 are correspondingly presented in tables 4 and 5 as follows:

TABLE 4

Titanium Dioxide Suspension Sample S1 (See FIG. 12a)

| | FDPM | DLS | X-ray |
|---|---|---|---|
| Mean (μm) | 0.310 | 0.314 | 0.318 |
| Std. Deviation (μm) | 0.118 | 0.112 | 0.115 |
| Volume Fraction | 0.0047 | 0.0045 (By Evaporation) | — |

TABLE 5

Titanium Dioxide Suspension Sample S2 (See FIG. 12b)

| | FDPM | DLS | X-ray |
|---|---|---|---|
| Mean (μm) | 0.318 | 0.375 | 0.359 |
| Std. Deviation (μm) | 0.079 | 0.143 | 0.145 |
| Volume Fraction | 0.0044 | 0.0045 (By Evaporation) | — |

Figure 16A:
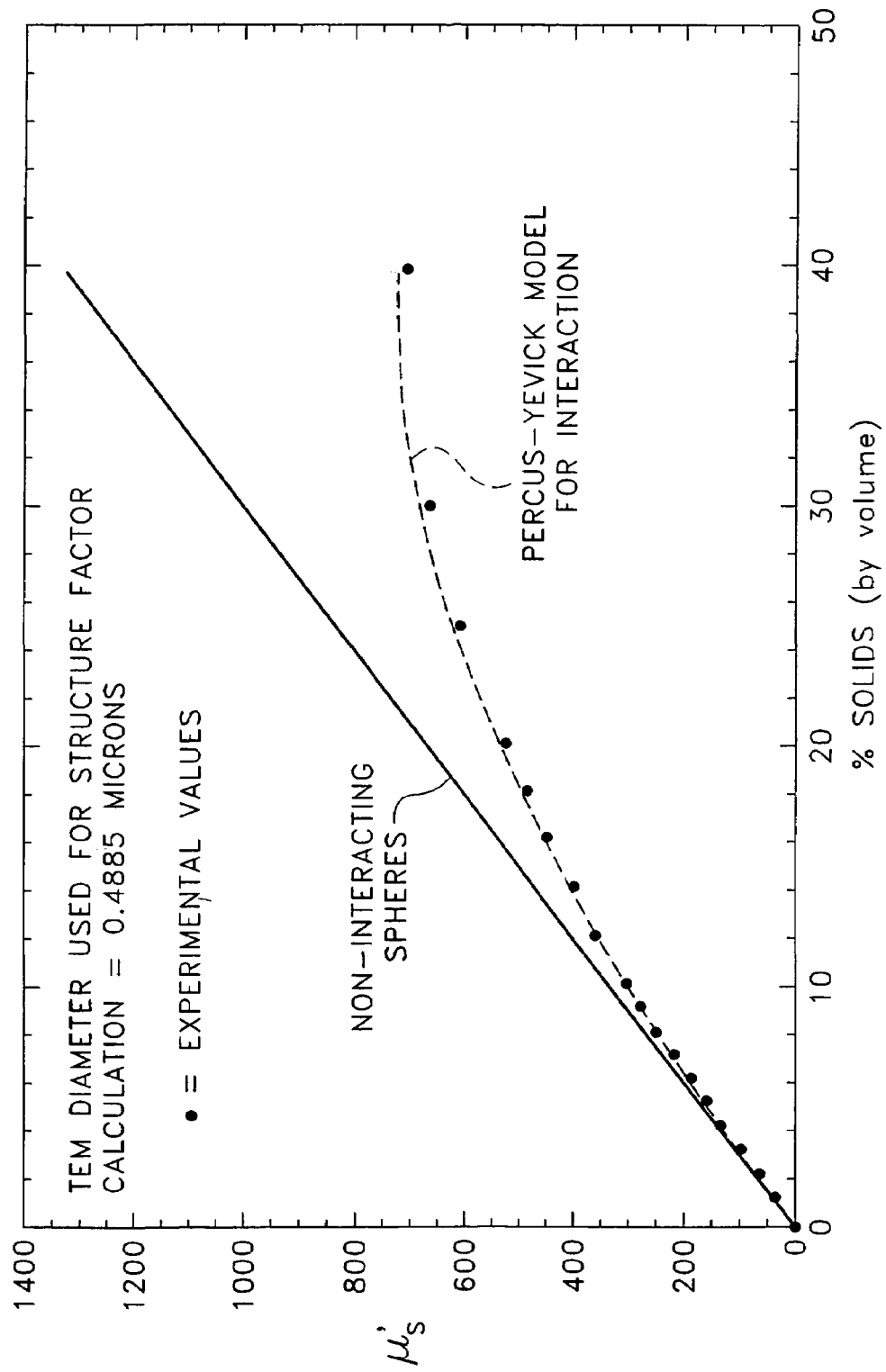
FIGS. 16*a*–16*c* are graphs comparing the relationship of the isotropic scattering coefficient with the percent solids by volume from polydisperse polystyrene particles in suspension having a mean diameter of about 0.4 micron, 0.2 micron, and 0.15 micron, respectively.
Figure 16B:
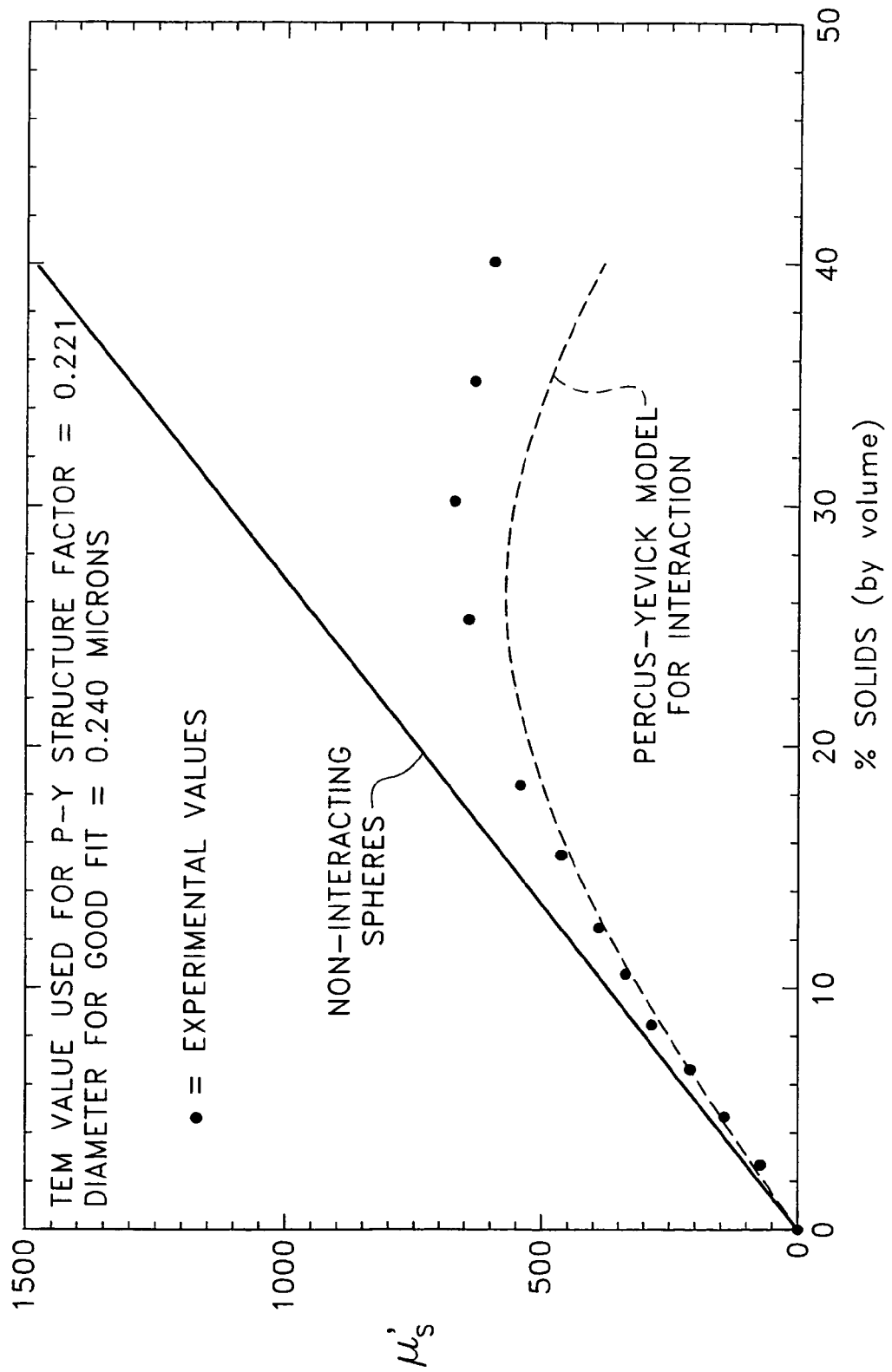
Figure 16C:
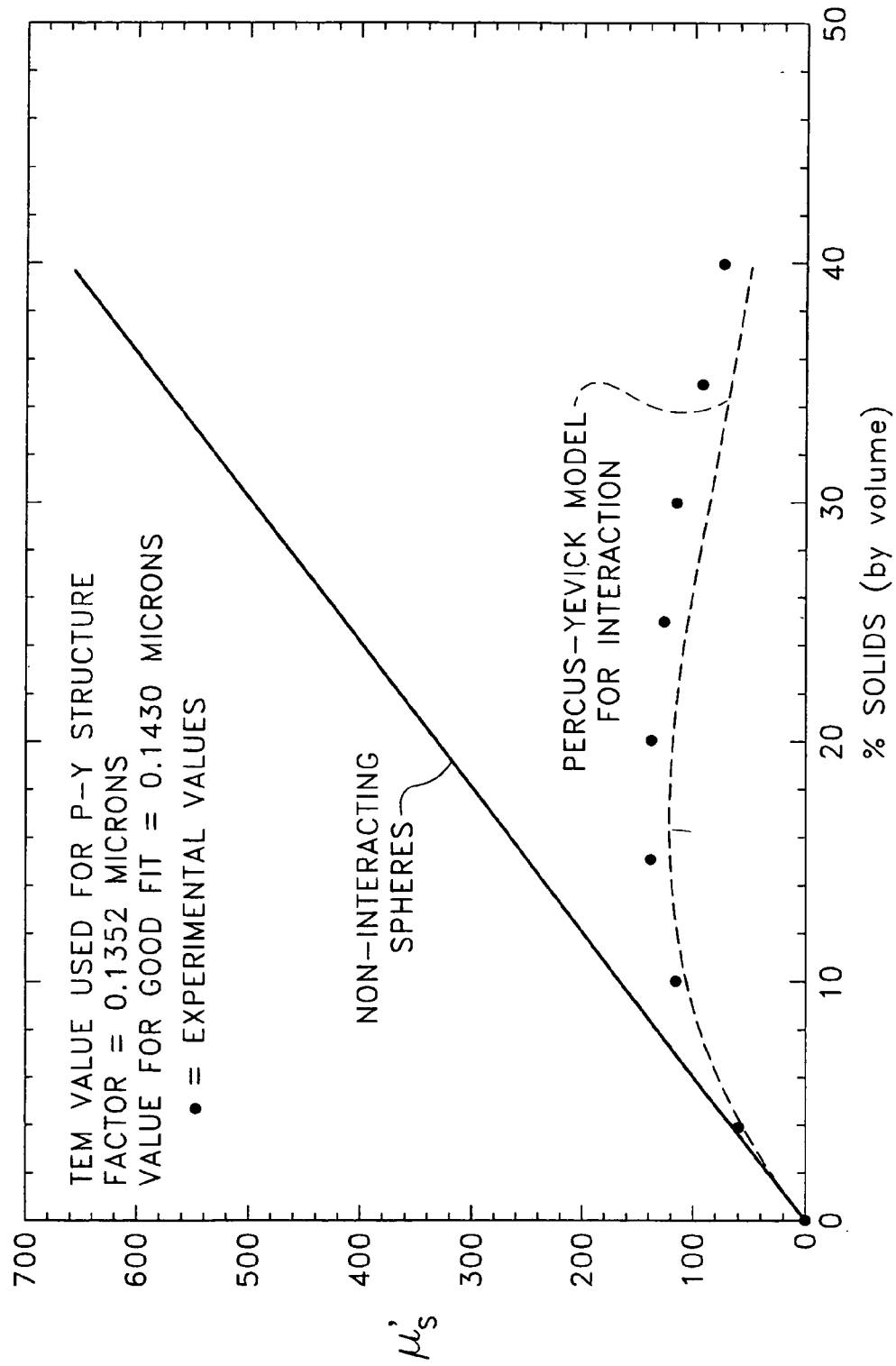

FIGS. 16a–16c comparatively illustrate the structure factor in terms of isotropic scattering coefficient (vertical axis) versus percent solids of particles by volume (horizontal axis). For each of FIGS. 16a–16c, the generally straight, solid line corresponds to the linear relationship of isotropic scattering coefficients to particle concentration when particle interactions are ignored (the structure factor equal to unity, S(q)=1); the circular symbols denote experimental measurements; and the dashed line indicates the nonlinear change of isotropic scattering coefficient with percent solids predicted by the P-Y hard sphere model. Notably, the P-Y model agrees well with the experimental data points, both illustrating a nonlinear relationship at higher concentrations. FIG. 16a shows the change in isotropic scattering coefficient with percent solids of the particles by volume at a wavelength of about 780 nanometers for a polydisperse polystyrene suspension with a mean particle diameter of about 0.4 micron. FIG. 16b shows the isotropic scattering coefficient at about 670 nanometers for a polydisperse polystyrene suspension having a mean particle diameter of about 0.15 micron. FIG. 16c illustrates the isotropic scattering coefficient at about a 670 nanometer wavelength for a polydisperse polystyrene suspension having a mean particle diameter of about 0.2 micron. It should be appreciated that the relationship between the isotropic scattering coefficient and particle concentration is generally linear at low concentration levels, and becomes increasingly nonlinear as the concentration level increases.

Figure 17A:
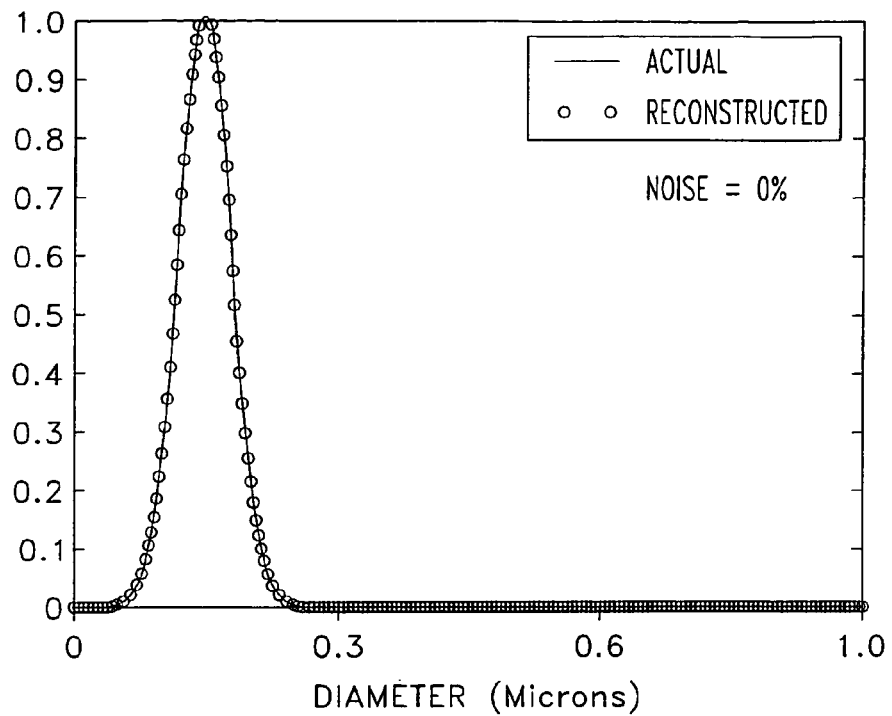
FIGS. 17*a*–17*c* are graphs depicting simulation results using a soft sphere particle-to-particle interaction structure factor model with simulated noise levels of 0%, 1%, and 5%, respectively.
Figure 17B:
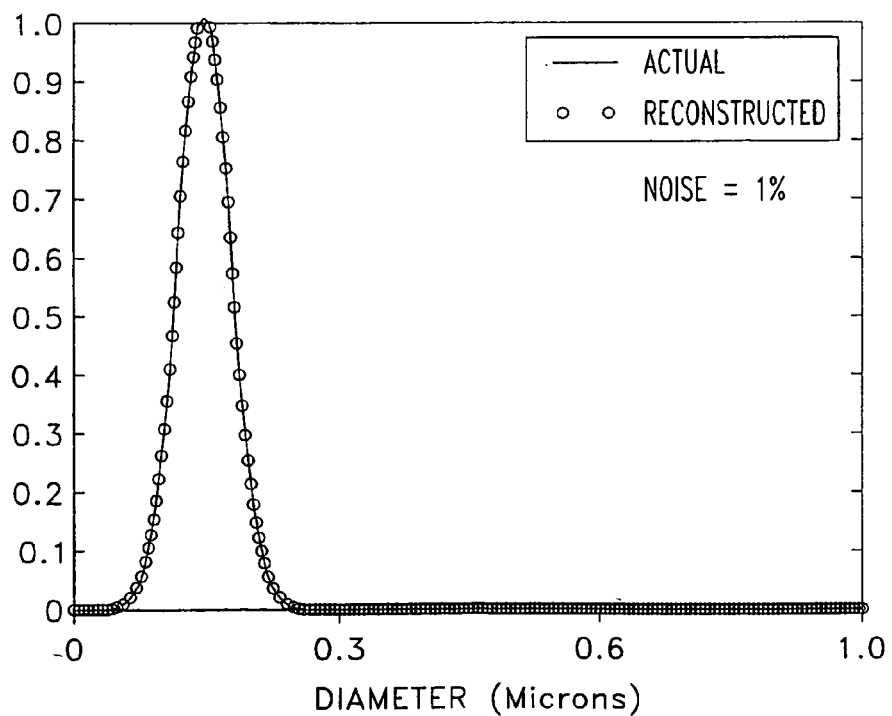
Figure 17C:
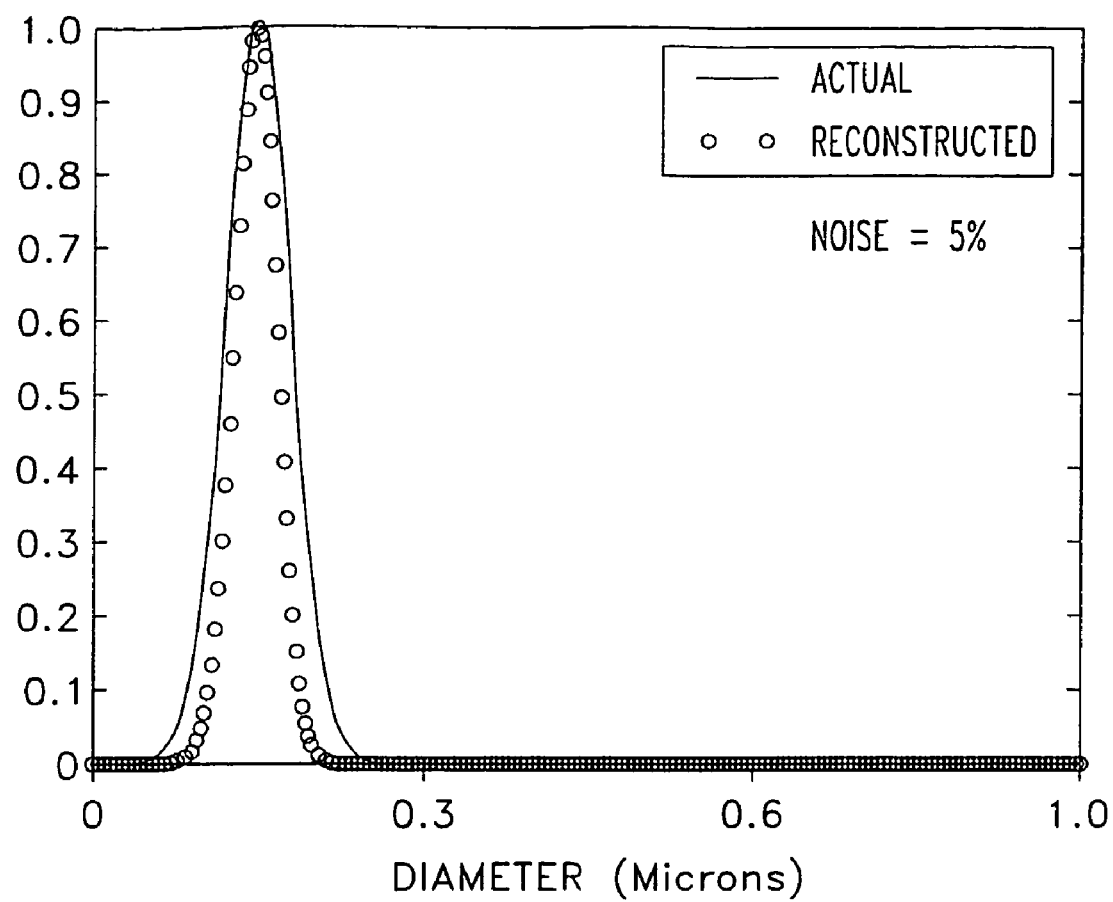

In yet another example, FIGS. 17a–17c illustrate the results of simulations of the soft sphere model for the structure factor. For these experiments, the inverse algorithm was applied to simulated measurements in the presence of various levels of noise. The particle size axis (the horizontal axis shown) was provided over a range between 15 nanometers and 1500 nanometers with the illustrated distributions being normalized to the peak value (vertical axis). Noise levels of 0%, 1%, and 5%, respectively, are shown in FIGS. 17a–17c. The results are tabulated in table 6 as follows:

TABLE 6

Summary of Recovered Distribution for Soft Sphere Model

|  | Actual Parameters | 0% Noise | 1% Noise | 5% Noise |
|---|---|---|---|---|
| Mean Diameter (nm) | 250 | 250 | 253.4 | 243.9 |
| Percent Error (%) | — | 0.00 | 1.36 | 2.44 |
| Deviation (nm) | 50 | 50 | 48.3 | 32.9 |
| Percent Error (%) | — | 0.00 | 3.4 | 34.2 |
| Volume Fraction | 0.31 | 0.31 | 0.314 | 0.291 |
| Percent Error (%) | — | 0.00 | 0.127 | 6.13 |
| $\Delta r$ (nm) | 25 | 25 | 22.7 | 28.6 |
| Percent Error (%) | — | 0.00 | 9.2 | 14.4 |

This table indicates that the soft sphere model facilitates a good recovery of mean and volume fraction values despite the presence of noise.

Because the photon migration measurements of the present invention depend upon differences in refractive indices between the dispersed particles and the surrounding fluid, the size distribution of a liquid droplet dispersion in a fluid medium is determinable through measurements of multiplied scattered light in accordance with the present invention. Thus, the determination of liquid droplet size distribution to assess dispersion processes is a significant problem in industry that may be addressed by the present invention.

In another embodiment, particle analysis techniques of the present invention include monitoring processes involving genetically engineered microbes. For example, the production of insulin in the granules of genetically engineered E. coli bacteria may be monitored to provide rapid feedback for optimization of the insulin production process.

Also, it should be appreciated that the present invention finds application in many process involving the distribution of fine particles, including, but not limited to: processes involving a dispersion of liquid or solid particles in a fluid medium; chemical reactions having particles of mixed phases (such as solids and liquid droplets dispersed together in a common fluid medium); and the mechanical formation of particles.

All publications, patents and patent applications cited in this specification are herein incorporated by reference as if each individual publication, patent, or patent application were specifically and individually indicated to be incorporated by reference. Copending U.S. patent application Ser. No. 08/747,112, filed 8 Nov. 1996, and 60/050,809, filed 26 Jun. 1997 are hereby incorporated by reference as if set-forth completely herein. While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of particle analysis, comprising:
    (a) exposing a number of particles in suspension to an incident light with a predetermined time-varying intensity, the particles being sufficiently close to one another to multiply scatter light;
    (b) detecting multiply scattered light from the particles in response to the incident light to determine a first value corresponding to an observed isotropic scattering coefficient of the particles;
    (c) establishing an estimate corresponding to at least one of volume fraction or size distribution of the particles;
    (d) calculating a second value from the estimate, the second value corresponding to a calculated isotropic scattering coefficient;
    (e) comparing the first and second values to establish an error;
    (f) changing the estimate;
    (g) repeating said calculating, comparing, and changing until the error reaches a desired minimum and;
    (h) controlling a process as a function of the estimate.

2. The method of claim 1, wherein the incident light includes a number of different wavelengths of light, the first value is determined for each of the wavelengths, and said establishing, said calculating, said comparing, and said changing are performed for each of the different wavelengths.

3. The method of claim 1, wherein the estimate corresponds to one of a number of parameters for an expected form of the size distribution.

4. The method of claim 3, wherein the incident light includes a number of different wavelengths of light, the first value is determined for each of the wavelengths, the parameters correspond to a Weibull distribution, and said calculating includes:
    (i) establishing a number of particle size increments;
    (ii) determining a scattering efficiency and a mean cosine of scattering angle as a function of the wavelengths and the increments; and
    (iii) performing a first summation over a range of the particle sizes for each of the wavelengths, the first summation having the parameters, the scattering efficiency, and the mean cosine of scattering angle as arguments.

5. The method of claim 4, wherein said comparing includes performing a second summation over a range of the wavelengths, the second summation including a numerical difference between the first and second values as an argument.

6. The method of claim 4, wherein said changing includes updating the parameters as a function of the wavelengths, the first and second values, and a third value corresponding to mass of the particles.

7. A system for analyzing a number of particles suspended in a medium in sufficient concentration to multiply scatter light comprising:
    a light source with a predetermined time-varying intensity configured to expose the medium to a number of different predetermined wavelengths of incident light;

a first sensor spaced apart from said source, said first sensor being configured to provide a first detection signal corresponding to detected light, the detected light being multiply scattered by the particles;

a processor responsive to the first detection signal and being configured to receive an exposure signal corresponding to said incident light, said processor being configured to generate: (a) a number of comparison signals each corresponding to a difference with respect to time between the detected light and the incident light for a corresponding one of the wavelengths, (b) a number of scattering signals each correspondingly determined from the comparison signals and each corresponding to an observed isotropic scattering coefficient of the medium for a different one of the wavelengths, and (c) an output signal indicative of one of size distribution or volume fraction of the particles, said output signal being determined as a function of said scattering signals; and an output device responsive to said output signal to provide an output corresponding to the size distribution or volume fraction of the particles.

8. The system of claim 7, further comprising a reaction vessel containing the particles and medium, and wherein said output device includes a control element operatively coupled to said reaction vessel and responsive to said output to regulate a process involving the particles.

9. The system of claim 7, wherein said processor is further configured to determine said size distribution or volume fraction as a function of mass of the particles.

10. The system of claim 7, further comprising a second sensor providing a second detection signal, said comparison signals being determined as a function of said first and second detection signals for each of the wavelengths.

11. The system of claim 7, wherein said processor further determines a structure factor indicative of particle-to-particle interactions, said structure factor varying in accordance with concentration of the particles in the medium.

12. The system of claim 7, wherein said processor is configured to generate a particle interaction signal representative of particle-to-particle interactions that vary with particle concentration and influence light scattering behavior of the particles.

13. A system for analyzing a number of particles suspended in a medium in sufficient concentration to multiply scatter light, comprising:
(a) a light source with a predetermined time-varying intensity configured to expose the medium to a number of different wavelengths of light;
(b) a sensor spaced apart from the source, said sensor being configured to provide a detected light signal corresponding to multiply scattered light from the particles at the different wavelengths in response to exposure to said source;
(c) a processor responsive to said detected light signal, said processor including a calculation means for generating an output signal corresponding to at least one of particle size distribution or volume fraction in accordance with an observed isotropic scattering coefficient of the medium determined from said detected light signal, said calculation means including a means for iteratively determining a structure factor from an estimate corresponding to at least one of said particle size distribution or said volume fraction, said structure factor being representative of particle interactions that influence light scattering behavior of said particles; and (d) an output device responsive to said output signal to provide an output corresponding to at least one of said size distribution or said volume fraction.

14. The system of claim 13, further comprising a reaction vessel containing the particles and the medium, and wherein said output device includes a control element operatively coupled to said reaction vessel and responsive to said output to regulate a reaction involving the particles.

15. The system of claim 13, wherein said calculation means includes an estimating means for iteratively determining said size distribution or said volume fraction as a function of mass of the particles.

16. The system of claim 13, wherein said structure factor is dependent on said particle size distribution and said particle volume fraction, and corresponds to a P-Y hard sphere model.

17. The system of claim 13, wherein said calculation means includes a number of parameters corresponding to a Weibull distribution.

18. A method of particle analysis, comprising:
(a) exposing a medium with a number of suspended particles to a number of light wavelengths, the wavelengths each being intensity-modulated at a predetermined frequency;
(b) detecting multiply scattered light from the medium in response to said exposing to characterize propagation of the multiply scattered light through the medium with a number of values, the values each corresponding to a different one of the wavelengths and each being representative of at least one of a phase or an amplitude of the multiply scattered light relative to the predetermined frequency; and
(c) providing an output determined from the values, the output corresponding to at least one of a particle size distribution, particle volume fraction, or a particle interaction parameter, the particle interaction parameter corresponding to a nonlinear relationship between particle concentration and an isotropic scattering coefficient for the particles.

19. The method of claim 18, further comprising controlling a process in accordance with the output.

20. The method of claim 18, wherein said providing includes determining the observed isotropic scattering coefficient and an absorption coefficient for the particles for each of the wavelengths from a corresponding one of the values.

21. The method of claim 18, wherein said providing includes:
(i) determining an observed isotropic scattering coefficient for the particles for each of the wavelengths from a corresponding one of the values;
(ii) establishing an estimate corresponding to at least one of the size distribution or the volume fraction;
(iii) determining a calculated isotropic scattering coefficient for each of the wavelengths from the estimate;
(iv) comparing the observed and calculated isotropic scattering coefficients to establish an error;
(v) changing the estimate; and
(vi) repeating said calculating, comparing, and changing until the error reaches a desired minimum.

22. The method of claim 21, wherein said providing includes selecting the estimate to generally maintain mass balance of the particles, and the estimate corresponds to an expected form of the size distribution of the particles.

23. The method of claim 21, wherein the calculated isotropic scattering coefficient is determined with an equation having an estimated product of the size distribution and the volume fraction as an argument.

24. The method of claim 18, wherein the particle interaction parameter is determined from a P-Y structure factor model.

25. A method of particle analysis, comprising:
(a) exposing a number of particles to a number of light wavelengths of predetermined time-varying intensity;
(b) detecting multiply scattered light from the particles in response to said exposing to determine a number of values each corresponding to a different one of the wavelengths, the values each being representative of a time-of-flight characteristic of the particles; and
(c) providing an output determined from the values, the output corresponding to at least one of a particle size distribution or volume fraction and being determined in accordance with a particle interaction parameter, the particle interaction parameter being representative of a nonlinear relationship between particle concentration and an isotropic scattering coefficient for the particles.

26. The method of claim 25, wherein the particles are suspended in a fluid medium and further comprising controlling a process in accordance with the output.

27. The method of claim 25, wherein the particles have a concentration in the fluid medium of at least about 10% by volume.

28. The method of claim 25, wherein said determining includes calculating at least one of volume fraction and size distribution of the particles in the fluid.

29. The method of claim 25, wherein the particle interaction parameter is determined from the Percus-Yevick hard sphere model.

30. The method of claim 29, wherein said calculating includes adjusting the hard sphere model to account for forces between the particles.

31. A method of analysis, comprising:
(a) exposing a fluid to an incident light, the fluid having a number of suspended particles therein, the suspended particles being sufficiently concentrated in the fluid to scatter light;
(b) detecting multiply scattered light in response to said exposing to determine a time-based value characteristic of propagation time of the multiply scattered light through the fluid;
(c) determining a quantity as a function of the value, the quantity corresponding to an isotropic scattering coefficient; and
(d) providing an output corresponding to at least one of volume fraction, particle size distribution, or a particle interaction parameter, the particle interaction parameter corresponding to particle-to-particle interactions influencing light scattering behavior of the particles, said providing including calculating a number representative of the isotropic scattering coefficient as a function of an estimate corresponding to the volume fraction and the size distribution.

32. The method of claim 31, further comprising controlling a process in which the particles are altered by utilizing the output as a feedback variable.

33. The method of claim 31, wherein said providing includes establishing an estimate corresponding to volume fraction and the size distribution and determining the particle interaction parameter as a function of the estimate.

34. The method of claim 33, further comprising constraining the estimate to maintain mass balance.

35. The method of claim 31, wherein the incident light is intensity modulated at a predetermined frequency, and said determining includes comparing the incident light and the scattered light to determine the value, and the value is representative of a relative phase or amplitude of the scattered light for the predetermined frequency.

36. The method of claim 35, wherein said detecting includes detecting the scattered light with a second sensor spaced apart from the first sensor by a separation distance and said determining includes calculating the quantity in accordance with the separation distance.

37. The method of claim 35, wherein said providing includes determining the volume fraction or size distribution in accordance with the diffusion equation for multiply scattered light.

38. The method of claim 31, wherein the particle interaction parameter is determined from a P-Y structure factor model.

39. A system for analyzing a number of particles suspended in a medium in sufficient concentration to multiply scatter light, comprising:
a light source configured to expose the medium to a number of different predetermined wavelengths of incident light each having a predetermined time-varying intensity;
a first sensor spaced apart from said source, said first sensor being configured to provide a first detection signal corresponding to detected light, the detected light being multiply scattered by the particles;
a processor responsive to said first detection signal and being configured to receive an exposure signal corresponding to said incident light, said processor being configured to generate: (a) a number of propagation signals by comparing said first detection signal and said exposure signal for each of said wavelengths, said propagation signals each characterizing time of flight of the detected light through the medium resulting from multiple scattering by the particles for a corresponding one of said wavelengths, (b) a number of scattering signals each corresponding to an isotropic scattering coefficient of the medium and being determined from a corresponding one of said propagation signals, and (c) an output signal indicative of at least one of size distribution or volume fraction of the particles, said output signal being determined from said scattering signals and a structure factor, said structure factor accounting for particle-to-particle interactions influencing light scattering behavior of the particles; and
an output device responsive to said output signal to provide an output corresponding to said size distribution or said volume fraction of the particles.

40. The system of claim 39, wherein said processor is further configured to determine said size distribution or said volume fraction as a function of mass of the particles.

41. The system of claim 39, further comprising a second sensor providing a second detection signal, said scattering signals being determined as a function of said first and second detection signals for each of the wavelengths.

42. The system of claim 39, wherein said structure factor corresponds to a P-Y hard sphere structure factor model.

43. The system of claim 39, wherein said processor further generates an absorption signal corresponding to an absorption coefficient of the medium and determines said absorption signal from said propagation signal.

44. A method of particle analysis, comprising:
(a) exposing a number of particles to a number of light wavelengths of predetermined time-varying intensity;
(b) detecting multiply scattered light from the particles in response to said exposing to determine a number of time-based propagation characteristics of the particles each corresponding to a different one of the wavelengths; and (c) calculating an observed isotropic scattering coefficient for each of the wavelengths from the characteristics;

(d) determining a calculated isotropic scattering coefficient for each of the wavelengths from an estimate of at least one of particle size distribution or particle volume fraction;

(e) comparing the observed isotropic scattering coefficient and calculated isotropic scattering coefficient for each of the wavelengths to establish and error;

(f) adjusting the estimate and repeating said determining and said comparing until the error reaches a desired minimum; and (g) providing an output corresponding to at least one of the particle size distribution, particle volume fraction, or a particle interaction parameter.

45. The method of claim 44, wherein said determining includes establishing the particle interaction parameter as a function of the particle volume fraction and the particle size distribution.

46. The method of claim 45, wherein the particle interaction parameter corresponds to the P-Y hard sphere structure factor.

47. The method of claim 46, wherein the calculated isotropic scattering coefficient is determined with an equation having the structure factor and an estimated product of the size distribution and the volume fraction as arguments.

48. The method of claim 44, wherein the particles include liquid droplets dispersed in a fluid medium, the droplets and the medium having different indices of refraction.

* * * * *